(12) United States Patent
Takeuchi et al.

(10) Patent No.: US 8,853,487 B2
(45) Date of Patent: Oct. 7, 2014

(54) DISPOSABLE ABSORBENT ARTICLE WITH TEMPERATURE CHANGING LAYER

(75) Inventors: Tomonari Takeuchi, Shikokuchuo (JP); Yuki Horie, Shikokuchuo (JP); Sayaka Kozai, Shikokuchuo (JP)

(73) Assignee: Daio Paper Corporation, Ehime (JP)

( * ) Notice: Subject to any disclaimer, the term of this patent is extended or adjusted under 35 U.S.C. 154(b) by 538 days.

(21) Appl. No.: 12/810,587

(22) PCT Filed: Dec. 26, 2008

(86) PCT No.: PCT/JP2008/073763
§ 371 (c)(1), (2), (4) Date: Jun. 25, 2010

(87) PCT Pub. No.: WO2009/084642
PCT Pub. Date: Jul. 9, 2009

(65) Prior Publication Data
US 2010/0280472 A1  Nov. 4, 2010

(30) Foreign Application Priority Data

Dec. 28, 2007 (JP) ................ 2007-340939
Feb. 29, 2008 (JP) ................ 2008-049943
Feb. 29, 2008 (JP) ................ 2008-051292
Feb. 29, 2008 (JP) ................ 2008-051294

(51) Int. Cl.
*A61F 13/15* (2006.01)
*A61F 13/20* (2006.01)
*A61L 15/42* (2006.01)
*A61F 13/42* (2006.01)
*A61L 15/60* (2006.01)

(52) U.S. Cl.
CPC ............... *A61F 13/42* (2013.01); *A61L 15/42* (2013.01); *A61L 15/60* (2013.01)
USPC ................ 604/361; 604/367; 604/385.01

(58) Field of Classification Search
USPC .................... 604/361, 367, 385.01
See application file for complete search history.

(56) References Cited

U.S. PATENT DOCUMENTS 5,269,775 A * 12/1993 Freeland et al. ......... 604/385.22
5,649,914 A   7/1997 Glaug
(Continued)

FOREIGN PATENT DOCUMENTS

| JP | 3830901 | 11/2006 |
| JP | 3922722 | 5/2007 |
| WO | WO2007091225 A1 | 8/2007 |

OTHER PUBLICATIONS

Extended European Search Report dated Dec. 21, 2011 related to counterpart Application No. EP08867323.1 based on International Appl. No. PCT/JP2008/073763; 5 pages.

*Primary Examiner* — Michele M Kidwell
(74) *Attorney, Agent, or Firm* — Renner, Kenner; Arthur M. Reginelli

(57) ABSTRACT

[Problems]
To provide a disposable absorbent article that can generate a large temperature change on a surface thereof.
[Means for Solving Problems]
A disposable absorbent article comprising, at an area including a crotch portion, an absorbent portion which has a liquid pervious face sheet (30), a liquid impervious sheet (11) and an absorbent structure (50) that is interposed therebetween is configured that on a surface of an absorbent body (56) having a high absorbent polymer at least in a face side layer thereof, a temperature changing substance (40) for cooling or heating urine by contact with the urine is sprinkled and that the urine, which has been cooled or heated by the temperature changing substance (40), can be absorbed and retained in the face side layer of the absorbent body (56).

20 Claims, 24 Drawing Sheets

(56) References Cited

U.S. PATENT DOCUMENTS

| | | |
|---|---|---|
| 5,681,298 A | 10/1997 | Brunner |
| 5,797,892 A | 8/1998 | Glaug |
| 6,565,549 B1 | 5/2003 | Allen |
| 6,572,600 B1 | 6/2003 | Roe |
| 6,642,427 B2 | 11/2003 | Roe |
| 6,989,471 B2 | 1/2006 | Schmidt |
| 7,537,586 B2 | 5/2009 | Kline |
| 2002/0169427 A1* | 11/2002 | Roe et al. ............... 604/361 |
| 2006/0142713 A1 | 6/2006 | Long |
| 2006/0142714 A1 | 6/2006 | Jackson |
| 2006/0142715 A1 | 6/2006 | Long |
| 2006/0224132 A1 | 10/2006 | Roe |

* cited by examiner (a)

(b)

DISPOSABLE ABSORBENT ARTICLE WITH TEMPERATURE CHANGING LAYER

TECHNICAL FIELD

The present invention relates to disposable absorbent articles, such as disposable diapers for use in toilet training and disposable absorbent pads.

BACKGROUND ART

Conventionally, disposable diapers for toilet training are generally devised in such a manner that excreted urine contacts the skin of a wearer to cause enhanced discomfort to the wearer due to wetness and thereby allowing the wearer to perceive his/her urination. However, such diapers may cause skin maceration and diaper rash. Accordingly, there have been developed technologies for allowing a wearer to perceive his/her urination while keeping urine away from the wearer.

Such technologies are typified by use of a substance such as sorbitol or the like which brings about a temperature change to urine when coming into contact with the urine (refer to Patent Documents 1 and 2, for example). Patent Document 1 suggests a technique that an absorbent structure (absorbent assembly) is provided with a member containing a temperature changing substance such as sorbitol or the like on the side of the structure facing the body of a wearer. In addition, Patent Document 2 suggests a technique that an absorbent core has on the surface thereof an element with a temperature changing substance such as sorbitol or the like between a permeable layer and an impermeable layer.

Patent Document 1: JP 3922722 A
Patent Document 2: JP 3830901 A

DISCLOSURE OF THE INVENTION

Technical Problems to be Solved

However, in the technique of Patent Document 1, urine cooled or heated by a temperature changing substance enters an absorbent structure and moves to the underside of the structure, and therefore there is a problem that the larger an amount of urine is excreted, the less a temperature change on an article surface contacting the body of a wearer becomes.

In addition, in the technique of Patent Document 2, urine cooled or heated by a temperature changing substance is temporarily retained in an impermeable layer, and therefore there is a problem that, when an larger amount of urine is excreted, the temperature changing substance cannot sufficiently cool or heat the urine, thereby generating a smaller degree of change from the urine temperature on urination.

Therefore, a main object of the present invention is to provide a disposable absorbent article that is capable of generating a large temperature change on a surface thereof.

Means to Solve the Problems

The present invention to solve the foregoing problems is as follows:
<Invention According to Claim 1>

A disposable absorbent article, comprising, at an area including a crotch portion, an absorbent portion which has a liquid pervious face sheet, a backside sheet and an absorbent structure that is interposed therebetween and that is formed by covering an absorbent body made of a high absorbent polymer and a fiber aggregate by an absorbent body covering sheet wherein between the absorbent body and the liquid pervious face sheet, a temperature changing layer is provided that contains a high absorbent polymer and a temperature changing substance for cooling or heating urine by contact with the urine, or the absorbent body is higher in density of the high absorbent polymer at a face side than at a back side, and has on the face side thereof a temperature changing layer that contains a temperature changing substance for cooling or heating urine by contact with the urine.
(Effect and Operation)

In the present invention, urine having passed through the face sheet on urination, is initially cooled or heated by the temperature changing substance, and then is promptly retained by the high absorbent polymer of the temperature changing layer disposed between the absorbent body and the liquid pervious face sheet or by the high absorbent polymer in the face side layer of the absorbent body, thereby transferring a temperature change to a wearer in an effective way. Then, after the high absorbent polymer in the temperature changing layer disposed between the absorbent body and the liquid pervious face sheet or the high absorbent polymer in the face side layer of the absorbent body has been saturated with absorbed urine, even if the urine cannot be sufficiently cooled or heated due to decrease in the temperature changing substance or the like, the urine is not absorbed or retained in the temperature changing layer disposed between the absorbent body and the liquid pervious face sheet or in the face side layer of the absorbent body, but is transferred to the backside of the absorbent body. That is, the sufficiently cooled or heated urine is absorbed and retained by the high absorbent polymer in the temperature changing layer disposed between the absorbent body and the liquid pervious face sheet or by the high absorbent polymer in the face side layer of the absorbent body, whereas the insufficiently cooled or heated urine is not retained in the temperature changing layer disposed between the absorbent body and the liquid pervious face sheet or in the face side layer of the absorbent body, but is moved to the backside of the absorbent body. Accordingly, the effect of cooling or heating by the temperature changing substance can be effectively transferred to the face side of the article, thereby to bring about a large temperature change to the face side of the article. Further, since the urine having passed through the face sheet is retained by the high absorbent polymer and is less prone to flow back to the skin of a wearer, it is possible to provide dry texture and cause less impact to the skin of a wearer.

In particular, if the absorbent body is higher in density of high absorbent polymer at the face side than at the back side, the absorbent body can retain a larger amount of cooled or heated urine at the face side to thereby generate a larger temperature change on the face side of the article.

In addition, if the temperature changing layer contains the high absorbent polymer, urine supplied to the temperature changing layer is cooled or heated by the temperature changing substance, and then is promptly absorbed by the high absorbent polymer without transferring heat to any other members. In addition to that, the urine cooled or heated by the temperature changing substance is retained at a position closer to the skin of a wearer to generate a further larger temperature change on the face side of the article.
<Invention According to Claim 2>

The disposable absorbent article according to Claim 1, wherein a periphery of a part having the temperature changing substance is separated from a periphery of the absorbent body and closer to a central side, and the part includes a portion having the high absorbent polymer at least on one of front-back-direction sides and width-direction sides thereof.

(Effect and Operation)

Since urine spreads in the absorbent article at an absorbent portion in a front-back direction and a width direction of the article, using such a structure makes it possible to absorb and retain effectively part of the urine cooled or heated at the part having the temperature changing substance and spreading around the part having the temperature changing substance by the high absorbent polymer. This brings about a larger temperature change in a wider range of the face side of the article.

<Invention According to Claim 3>

The disposable absorbent article according to Claim 2, wherein the liquid pervious face sheet is formed by a nonwoven fabric with a thickness of 0.5 mm or less and a basis weight of 10 to 40 g/m$^2$;

the absorbent body covering sheet is formed by crepe paper or a nonwoven fabric with a thickness of 0.2 mm or less and a basis weight of 5 to 25 g/m$^2$;

no other member exists at least at a part overlapping the part having the high absorbent polymer between the liquid pervious face sheet and the temperature changing layer;

the temperature changing substance cools urine by dissolving into the urine and causing an endothermic reaction, and has a solubility of 30 g or more in water of 100 ml at a temperature of 20° C. of 100 ml at a temperature of 20° C.;

the temperature changing substance has a basis weight of 300 to 800 g/m$^2$;

the part having the temperature changing substance has an area of 2,500 to 20,000 mm$^2$;

the temperature changing substance is capable of causing a total amount of change of heat quantity of 50 cal or more to the absorbent body;

the part having the temperature changing substance has a rate of change of heat quantity per unit area of 1 cal/cm$^2$ or more;

the high absorbent polymer has an absorption speed of 50 seconds or less;

the high absorbent polymer has a basis weight of 50 to 400 g/m$^2$; and the part having the high absorbent polymer has an area of 2,500 to 20,000 mm$^2$.

(Effect and Operation)

In the present invention, such a structure is preferably employed to use the temperature changing substance and the high absorbent polymer of the aforementioned kinds, performances and volumes. The absorbent speed here refers to a period of time required for a specimen of 2 g to absorb physiological saline of 50 g, and is measured in accordance with JIS K 7224-1996 (this remark also applies to the description hereinafter).

<Invention According to Claim 4>

The disposable absorbent article according to Claim 3, wherein a layer containing a water-soluble substance is provided as a lower layer below the temperature changing layer.

(Effect and Operation)

In the absorbent article of Patent Document 1, an absorbent assembly has a liquid pervious temperature changing member on a face side thereof, and therefore a moisture content such as urine excreted from the body of a wearer passes through a layer of the liquid pervious temperature changing member and then promptly moves to the absorbent assembly under the layer. Accordingly, the moisture content such as urine changed in temperature by contact with the temperature changing member are absorbed and retained by pulp or polymer in the absorbent assembly distant from the skin of the wearer, which cannot allow the wearer to sufficiently perceive the temperature change.

In addition, in the disposable absorbent article of Patent Document 2, a temperature changing element is formed by sandwiching a temperature changing substance between a liquid pervious layer and a liquid impervious layer. Accordingly, on first urination, urine moves over the surface of the liquid impervious layer in an X-Y plane and moistens the temperature changing substance, to thereby generate a temperature change efficiently and allow the wearer to perceive the temperature change sufficiently. However, if second and subsequent urination is repeated even though most of the temperature changing substance has been dissolved at the first urination and therefore cannot exert any longer a sufficient temperature changing effect, the urine is retained in the liquid impervious layer and is blocked from being absorbed into an absorbent core, thereby causing a problem of urine leakage or the like.

In contrast, if the absorbent article has a two-layer structure with the temperature changing layer and the layer containing a water-soluble substance as a lower layer below the temperature changing layer as stated above, the article allows the urine to retain temporarily in the layer above the layer containing the water-soluble substance, taking advantage of the fact that the layer containing the water-soluble substance takes a certain period of time to cause the water-soluble substance to be dissolved in a liquid on first urination. This prevents that the urine is instantly absorbed in the absorbent body. Accordingly, it is possible to let the temperature changing substance in the upper layer contacts sufficiently the urine to generate a secure temperature change and allow a wearer to perceive the temperature change in a reliable manner. In addition, the water-soluble substance is dissolved in urine on first urination, and therefore even if second or subsequent urination is repeated, the temperature changing substance does not interfere with absorption of the urine into the absorbent body or cause a problem of urine leakage or the like.

<Invention According to Claim 5>

The disposable absorbent article according to Claim 4, wherein the layer containing the water-soluble substance is constituted by a formed body mainly made from the water-soluble substance.

<Invention According to Claim 6>

The disposable absorbent article according to Claim 5, wherein the layer containing the water-soluble substance is constituted by a liquid pervious sheet-like object with the water-soluble substance supported.

<Invention According to Claim 7>

The disposable absorbent article according to Claim 3, wherein, out of a central portion of the absorbent body in the width direction, the temperature changing substance is welded to at least a part ranging from the crotch portion to the ventral side portion, and the temperature changing substance is not welded around the temperature changing substance welded part of the absorbent body.

(Effect and Operation)

With conventional techniques, an absorbent article contains a temperature changing substance in powder and granular form and in an unfixed state, and therefore the temperature changing substance may move from a predetermined position during transportation of the product or during use of the product, whereby the temperature changing substance is undersupplied with urine or a temperature change is not sufficiently transferred to the body of a wearer, resulting in an inadequate temperature change.

In addition, even if the temperature changing substance does not move, the conventional techniques may cause a problem that the part containing the temperature changing substance does not fit to the body of a wearer due to deformation by wrinkles or the like, and therefore the part containing the temperature changing substance is undersupplied with urine, whereby an adequate temperature change does not take place or a temperature change is not sufficiently transferred to the body of a wearer.

In contrast, if, out of the central portion of the absorbent body in the width direction, the temperature changing substance is welded to at least the part ranging from the crotch portion to the ventral side portion as stated above, the temperature changing substance can be certainly retained at least in the part. In addition, the temperature changing substance-welded part of the absorbent body is higher in firmness (solidity) than the temperature changing substance-unwelded part around the same. Therefore, the temperature changing substance-welded part retaining certainly the temperature changing substance is less prone to be deformed by wrinkles, buckling, or the like, whereby the part ranging from the crotch portion to the ventral side portion can be fitted favorably to the body of a wearer. Consequently, according to the present invention, the temperature changing substance can be more effectively supplied with a sufficient amount of urine to generate a desired temperature change, and the temperature change can be transferred to the body of a wearer in an effective way. In the present invention, the term "welding (welded)" refers to a condition of the temperature changing substance that is fused and attached to an object (absorbent body), and then solidified and fixed to the object. In addition, the crotch portion refers to a central portion in the front-back direction ranging from the waist end edge of a ventral side portion to the waist end edge of a back side portion of the absorbent article in an open state. The ventral side portion and the back side portion refer to parts on the front side and back side of the crotch portion, respectively.

<Invention According to Claim 8>

The disposable absorbent article according to Claim 7, wherein assuming that a product length defined as a front-back direction length ranging from the waist end edge of the ventral side portion to the waist end edge of the back side portion of the absorbent article in an open state is designated as L, the absorbent body is provided at least in a range of 0.15 to 0.80L from the waist side end edge of the ventral side portion to the crotch side, and the temperature changing substance-welded part is provided at least in a range of 0.25 to 0.45L from the waist side end edge of the ventral side portion to the crotch side.

(Effect and Operation)

By employing such dimensions as stated above, the temperature changing substance-welded part can be located to be suited for positions of urination of male and female wearers. That is, on urination, urine can contact certainly the temperature changing substance-welded part.

<Invention According to Claim 9>

The disposable absorbent article according to Claim 8, wherein the temperature changing substance-welded part is shaped along the groin portion of a wearer so as to be wider than the groin portion and be further wider with increasing proximity to the waist side.

(Effect and Operation)

By shaping the temperature changing substance-welded part as stated above, the absorbent article is less prone to form longitudinal wrinkles at the crotch portion and wrinkles along the groin portion, thereby further increasing a fit to the body of a wearer from the crotch portion to the ventral side portion.

<Invention According to Claim 10>

The disposable absorbent article according to Claim 9, wherein the crotch portion of the absorbent body has a narrower portion along the legs, and if it is assumed that the absorbent body in an open state has a front-back direction length Y and a width X, the narrower portion has a front-back direction length of 0.2 to 0.3Y and a narrowest part of the narrower portion has a width of 0.6 to 0.75X, the waist side end edge of the temperature changing substance-welded part in the ventral side portion has a width of 0.4 to 0.7X, a crotch side end of the further wider portion of the temperature changing substance-welded part is located at the same position as the narrowest part of the narrower portion or is located closer to the ventral side than the former position, and a back end of the temperature changing substance-welded part is located at the same position as a back end of the narrower portion or is located closer to the back side than the former position, and the back end has a width of 0.7 times or less the width of the waist side end edge of the temperature changing substance-welded part in the ventral side portion, and the width is 0.5X or less.

(Effect and Operation)

Preferably, the crotch portion of the absorbent body has the narrower portion along the legs, which enhances a fit to the bases of the legs and the crotch portion and makes the crotch portion less prone to be longitudinally wrinkled. In that case, dimensions of those portions preferably fall within the ranges defined in this claim. Specifically, when the dimensions of the absorbent body fall within the foregoing ranges, the absorbent body is prone to fit to the legs of a wearer. In addition, when the width of the waist side end edge of the welded part in the ventral side portion falls within the foregoing range and the crotch side end of the further wider part of the temperature changing substance-welded part is located in the foregoing range, it is possible to prevent effectively that the absorbent article is wrinkled along the groin portion due to a wearer's walking. Further, when the back end of the temperature changing substance-welded part falls within the foregoing range, there is no need to dispose the temperature changing substance unnecessarily at the gluteal portion that is less sensitive to temperature changes. Moreover, when the width of the back end of the temperature changing substance-welded part falls within the foregoing range, the crotch portion is preferably less prone to be longitudinally wrinkled.

<Invention According to Claim 11>

The disposable absorbent article according to Claim 3, wherein a heat-insulating layer is disposed between the absorbent structure and the backside sheet.

(Effect and Operation)

With conventional techniques, part of urine cooled or heated by the temperature changing substance moves to a portion closer to the outer surface of the article and is retained in the portion. Accordingly, the cooled urine is heated or the heated urine is cooled by influence of an outside air temperature, which causes a problem that a temperature change cannot be sufficiently transferred to a wearer to make an intended toilet training effect hard to obtain.

In contrast, if the backside of the absorbent structure is covered with the heat-insulating layer as stated above, urine having passed through the face sheet is cooled or heated by contact with the temperature changing substance and is retained in the absorbent body, and the temperature is transferred to the body of a wearer to cause the wearer to perceive his/her urination. Therefore, even if an outside air temperature is extremely high (in midsummer, near a heating apparatus in winter season) or is extremely low (outdoor in winter season or the like), the temperature of urine retained in the absorbent body can be maintained to provide a desired temperature change.

<Invention According to Claim 12>

The disposable absorbent article according to Claim 11, wherein the absorbent body is formed by a fiber aggregate with a fiber density of 2.25 to 6.75 g/m$^3$, the heat-insulating layer is formed by a fiber aggregate with a fiber density of 0.5 to 1.5 g/m$^3$, and the fiber density of the absorbent body is 4.5 times or more the fiber density of the heat-insulating layer.

(Effect and Operation)

If the absorbent body and the heat-insulating layer are configured as stated in this claim, urine absorbed in the absorbent body is less prone to move to the heat-insulating layer, whereby the urine changed in temperature can be retained in a portion closer to the body of the wearer. In addition, the heat-insulating layer can be less prone to have decrease in heat insulating performance due to urine retention.

<Invention According to Claim 13>

The disposable absorbent article according to Claim 12, wherein separately from the absorbent body, the heat-insulating layer is covered with a heat-insulating layer covering sheet made of a fiber aggregate with a higher fiber density than that of the heat-insulating layer.

(Effect and Operation)

If the heat-insulating layer is covered with such a fiber aggregate sheet, even if urine having passed through the absorbent body reaches the heat-insulating side, the urine is absorbed and retained in the fiber aggregate sheet and thus is less prone to be retained in the heat-insulating layer. This maintains heat-insulating performance of the heat-insulating layer.

<Invention According to Claim 14>

The disposable absorbent article according to Claim 13, wherein the heat-insulating layer covers an area of 50% or more of the backside surface of the absorbent body.

(Effect and Operation)

Although the heat-insulating layer may cover only part of the absorbent body (for example, only the crotch portion), the heat-insulating layer can cover an area of 50% or more of the backside surface of the absorbent body to thereby exert a more reliable and adequate heat-insulating effect.

Effect of the Invention

As stated above, the present invention provides a disposable absorbent article with advantages of generating a large temperature change on the face side of the article, and the like.

BEST MODE FOR CARRYING OUT THE INVENTION

An embodiment of the present invention will be described below, taking an underpants type disposable diaper (toilet training pants) as an example. Needless to say, however, the present invention is also applicable to tape-type disposable diapers, pad-type absorbent articles, and others.

<Example of Basic Structure of Underpants Type Disposable Diaper>

FIGS. 1 to 9 show one example of an underpants type disposable diaper. In the following description, the term "front-back direction" refers to a direction (longitudinal direction) that links a ventral side (front side) to a back side (rear side); the term "width direction" refers to a direction (right-left direction) orthogonal to the front-back direction; and the term "up-down direction" refers to a direction that becomes orthogonal to an abdomen direction when the diaper is being used, that is, when the diaper is folded in two such that a ventral portion and a back portion of the diaper are overlapped, in other words, a direction that links a waist opening WO to a crotch portion.

The underpants type disposable diaper has a ventral side outer sheet 12F covering a ventral side of an abdomen of a wearer, and a back side outer sheet 12B covering a back side of the same. The ventral side outer sheet 12F and the back side outer sheet 12B are welded and joined together in the entire up-down direction at both width-direction side edges by heat sealing, ultrasonic welding or the like, thereby to form a barrel shaped abdomen portion 100. Reference numeral 12A denotes individual welding sections, and welded section groups 12A constitutes side seal sections. As illustrated, if the back side outer sheet 12B extends under the welded sections 12A, the back side outer sheet 12B can be processed with heat sealing or the like uniformly in an up-down direction range containing such an extended section, so that the back side extended portion 14 can be provided with extended welded sections 12E. By providing the extended welded sections 12E, it is possible to prevent that second elongated resilient and elastic members 16 are drawn in at the back side extended portion 14 as described later. In this case, in a general joint pattern, the welded sections 12A are constituted by a series of small welding points for a lower proportion of a welded area, in consideration of ease of tearing off the diaper at the side. However, since there is no need to consider ease of tearing for the extended welded sections 12E, the proportion of a welded area may be made higher at the extended welded sections 12E than at the welded sections 12A, so that the second elongated resilient and elastic members 16 can be welded and fixed in a reliable manner. In addition, the extended welded sections 12E may be welded in a curved line at an edge of a gluteal cover section 14C to thereby prevent that the second elongated resilient and elastic members 16 are drawn in at the gluteal cover section 14.

In addition, in the abdomen portion 100, an inner body 200 is connected with a hot melt adhesive or the like at a front end portion thereof to an inner surface of a central portion of the ventral side outer sheet 12F in the width direction, and is connected with a hot-melt adhesive or the like at a back end portion thereof to an inner surface of a central portion of the back side outer sheet 12B in the width direction. The ventral side outer sheet 12F and the back side outer sheet 12B are not connected but separated from each other at the crotch side. A separation distance Y may be about 150 to 250 mm. Although not shown, as another embodiment, the abdomen portion 100 may have the ventral side outer sheet 12F and the back side outer sheet 12B connected at the crotch portion, that is, may be covered seamlessly from the ventral side to the back side with a single-piece outer sheet.

As seen from FIGS. 7 and 8, an upper opening of the abdomen portion 100 constitutes the waist opening WO through which the abdomen of a wearer passes, and sections surrounded by a lower edge of the abdomen portion 100 and side edges of the inner body 200 on the both sides of the inner body 200 in the width direction constitute leg openings LO through which the legs of a wearer pass. The diaper is formed in the shape of a sand clock when the diaper is torn off at the welded sections 12A and opened as shown in FIG. 1. The inner body 200 extends and covers from the back side through the crotch portion to the ventral side, and is intended to receive excreted objects, and absorb and retain body liquids. The abdomen portion 100 is designed to hold the inner body 200 with respect to a wearer.

(Outer Sheet)

The ventral side outer sheet 12F and the back side outer sheet 12B are each formed by sticking together two sheet-like materials 12 and 12, as shown in FIGS. 4 and 5. The inner sheet-like material 12 positioned on the inside of the outer sheet extends to the edge of the waist opening WO, whereas the outer sheet-like material 12 positioned on the outside of the outer sheet wraps around the waist side edge of the inner sheet-like material 12 and is folded back inside. A folded section 12r of the outer sheet-like material 12 extends so as to cover an upper side of the waist side edge of the inner body 200, and is fixed with a hot-melt adhesive or the like to an opposite surface. The sheet-like materials 12 only need to be capable of being welded and have no particular limitation in other respects, but preferably use a nonwoven fabric. Such a nonwoven fabric has no particular limitation in raw fibers therefor. For example, the raw fibers may be any of synthetic fibers based on olefin such as polyethylene or polypropylene, polyester, polyamide or the like, recycled fibers such as rayon or cupra, natural fibers such as cotton or the like, mixed or composite fibers of two or more of the foregoing fibers. Further, the nonwoven fabric may be produced by any processing method. For example, the processing method may be any of known methods such as a spun lace method, spun bonding method, thermal bonding method, melt-blown method, needle punching method, air-through method, point bonding method, and the like. If any nonwoven fabric is used, the nonwoven fabric preferably has a fiber basis weight of about 10 to 30 g/m$^2$.

In addition, for an enhanced fit at the abdomen portion, the ventral side outer sheet 12F and the back side outer sheet 12B have elongated resilient and elastic members 15 to 19 such as rubber threads at a predetermined extension ratio between the two sheet-like materials 12 and 12. The elongated resilient and elastic members 15 to 19 may use synthetic rubber or natural rubber. Using a hot-melt adhesive or heat sealing or ultrasonic attachment, the two sheet-like materials 12 and 12 can be attached together in the outer sheets 12F and 12B and the elongated resilient and elastic members 15 to 19 can be sandwiched and fixed between the sheet-like materials 12 and 12. It is not preferred to fix the entire outer sheets 12F and 12B firmly because this deteriorates these sheets in texture. As a preferred combination, the elongated resilient and elastic members 15 to 19 are firmly attached and other parts are not attached or are weakly attached.

More specifically, the back side outer sheet 12B has a back side main portion 13 corresponding to an up-down direction range of the side seal section with the welded sections 12A constituted by welding points, and a back side extended portion 14 extending under the back side main portion 13. The back side extended portion 14 has a width-direction intermediate section 14M overlapping the inner body 200, and has a gluteal cover section 14C extending from both sides of the width-direction intermediate section 14M.

A shape of the back side extended portion 14 can be decided as appropriate. In the illustrated example, the back side extended portion 14 has an upper end thereof extended under the back side main portion 13 with the same width as that of the back side main portion 13 and a lower end thereof made narrower with proximity to the crotch side. Alternatively, a part of the back side extended portion 14 with the same width as that of the back side main portion 13 may be omitted. In such a configuration, an outer edge 14e of the gluteal cover section 14C in the width direction is shaped in a straight line or a curved line approaching the inner body 200 with proximity to the crotch portion. This shape makes it easy to cover the gluteal part of a wearer.

Dimensions of the back side extended portion 14 can be decided as appropriate. More preferably, as shown in FIG. 6, the gluteal cover section 14C has a length 14x of 80 to 160 mm in the width direction (a maximum separation distance in the width direction between an outer edge 14e of the gluteal cover section 14C and a side edge of the inner body 200 in the width direction), and the gluteal cover section 14C has a length 14y of 30 to 80 mm in the up-down direction (an extended length). In addition, assuming that an area of a square defined by a widest side of the back side extended portion 14 in the width direction and a widest side of the back side extended portion 14 in the up-down direction is designated as S, the area of the back side extended portion 14 is preferably about 20 to 80% of S, in particular preferably about 40 to 60% of S, thereby achieving enhancement in outer appearance and fit at the gluteal portion.

The back side main portion 13 is divided conceptually in the up-down direction into an upper end portion (waist portion) W and a lower portion U under the same. Although dimensions of these portions vary depending on the size of the diaper, generally, the upper end portion W may be 15 to 80 mm long in the up-down direction, and the lower portion U may be 35 to 220 mm long in the up-down direction.

In the upper end portion (waist portion) W of the back side main portion 13, a plurality of back side waist resilient and elastic members 17 is continuously fixed in the entire width direction between an inner surface of the inner sheet-like material 12 and an outer surface of a folded section 12r of the outer sheet-like material 12, at up-down direction intervals therebetween and in a state of being extended in the width direction at a predetermined extension ratio. In addition, out of the back side waist resilient and elastic members 17, one or more members disposed in a section adjacent to the lower portion U of the back side main portion 13 may overlap the inner body 200, or may be disposed on both sides of the lower portion U in the width direction except for a central portion in the width direction overlapping the inner body 200. As the back side waist resilient and elastic members 17, about 3 to 22 rubber threads with a fineness of about 155 to 1,880 dtex, in particular about 470 to 1,240 dtex (in the case of synthetic rubber. For natural rubber, about 0.05 to 1.5 mm$^2$, particularly about 0.1 to 1.0 mm$^2$, in cross-section area), are preferably fixed at intervals of 4 to 12 mm at an extension ratio of about 150 to 400%, in particular about 220 to 320%. In addition, the back side waist resilient and elastic members 17 do not need to be all the same in fineness and extension ratio, and may be different in fineness and extension ratio between the upper and lower portions of the back side waist portion, for example.

In addition, in the lower portion U of the back side main portion 13, except for a central portion overlapping the inner body 200 in the width direction, a plurality of first elongated resilient and elastic members 15 is continuously fixed in the entire width direction to sections above and on both sides of the central portion overlapping the inner body 200 in the width direction, between an outer surface of the inner sheet-like material 12 and an inner surface of the outer sheet-like material 12, at up-down direction intervals therebetween and in a state of being extended in the width direction at a predetermined extension ratio.

As the first elongated resilient and elastic members 15, about 5 to 30 rubber threads with a fineness of about 155 to 1,880 dtex, in particular about 470 to 1,240 dtex (in the case of synthetic rubber. For natural rubber, about 0.05 to 1.5 mm$^2$, particularly about 0.1 to 1.0 mm$^2$, in cross-section area), are preferably fixed at intervals of 1 to 15 mm, in particular 3 to 8 mm, at an extension ratio of about 200 to 350%, in particular about 240 to 300%.

Further, in the back side extended portion 14, except for a central portion overlapping the inner body 200 in the width direction, a plurality of second elongated resilient and elastic members 16 is continuously fixed in the entire width direction to sections (at least covering the entire gluteal cover section 14C) on the both sides of the central portion overlapping the inner body 200, between an outer surface of the inner sheet-like material 12 and an inner surface of the outer sheet-like material 12, at up-down direction intervals and in a state of being extended in the width direction at a predetermined extension ratio.

As the second elongated resilient and elastic members 16, about 2 to 10 rubber threads with a fineness of about 155 to 1,880 dtex, in particular about 470 to 1,240 dtex (in the case of synthetic rubber. For natural rubber, about 0.05 to 1.5 mm$^2$, particularly about 0.1 to 1.0 mm$^2$, in cross-section area), are preferably fixed at intervals of 5 to 40 mm, in particular 5 to 20 mm, at an extension ratio of 150 to 300%, in particular 180 to 260%.

Meanwhile, the ventral side outer sheet 12F is composed of only the ventral side main portion (corresponding to the up-down direction range of the side seal section with the welded sections 12A constituted by welding points), basically in the same manner as the back side main portion 13 of the back side outer sheet 12B. Therefore, the ventral side outer sheet 12F is formed in the shape of a rectangle extending along the abdomen direction, and has no extended portion unlike the back side outer sheet 12B with the back side extended portion 14.

Specifically, in an upper end portion (waist portion) W and a lower portion U of the ventral side outer sheet (ventral side main portion) 12F, a plurality of ventral side waist resilient and elastic members 18 is continuously fixed in the entire width direction between an inner surface of the inner sheet-like material 12 and an outer surface of a folded section 12r of the outer sheet-like material 12 of the upper end portion W, at up-down direction intervals therebetween and in a state of being extended in the width direction at a predetermined extension ratio. The ventral side waist resilient and elastic members 18 are preferably approximated as much as possible to the back side waist resilient and elastic members 17 in number, fineness, extension ratio, interval, and up-down direction arrangement pattern, but may be different. If the ventral side waist resilient and elastic members 18 are made different, a difference in number is 10 or less, preferably 5 or less; a difference in fineness is 1,880 dtex or less, preferably 470 dtex or less; a difference in extension ratio is 100% or less, preferably 40% or less; and a difference in interval is 10 mm or less, preferably 5 mm or less.

In addition, in the lower portion U of the ventral side outer sheet 12F (ventral side main portion), except for a central portion in the width direction overlapping the inner body 200, a plurality of third elongated resilient and elastic members 19 is continuously fixed in the entire width direction to sections above and on both sides of the central portion, between an outer surface of the inner sheet-like material 12 and an inner surface of the outer sheet-like material 12, at up-down direction intervals and in a state of being extended in the width direction at a predetermined extension ratio. The third elongated resilient and elastic members 19 may be disposed in part of the lower portion in the up-down direction, but are preferably disposed in the substantially entire lower portion (where contraction force acts entirely).

The third elongated resilient and elastic members 19 are preferably approximated as much as possible to the first elongated resilient and elastic members 15 in number, fineness, extension ratio, interval, and up-down direction arrangement pattern, but may be different. If the third elongated resilient and elastic members 19 are made different, a difference in number is 10 or less, preferably 5 or less; a difference in fineness 1,880 dtex or less, preferably 470 dtex or less; a difference in extension ratio 100% or less, preferably 40% or less; and a difference in interval 10 mm or less, preferably 5 mm or less.

Meanwhile, the ventral side outer sheet 12F in the illustrated embodiment is composed of only a section corresponding to the up-down direction range of the welded sections 12A. Alternatively, the ventral side outer sheet 12F may include a ventral side main portion corresponding to the up-down direction range of the welded sections 12A, and a ventral side extended portion extending under the ventral side main portion, as with the back side outer sheet 12B. Accordingly, the ventral side outer sheet 12F can be formed so as to fit to the legs of the wearer along the groin. In this case, an area of the ventral side extended portion accounts for preferably 10 to 80%, more preferably 20 to 50% of an area of the back side extended portion. The excessively large ventral side extended portion would undesirably deteriorate a fit property.

Meanwhile, as shown in the diagram, the first, second, and third elongated resilient and elastic members 15, 16, and 19 are preferably provided on the both sides in the width direction except for the central portion that overlaps the inner body 200 in the width direction, because the inner body 200 and the outer sheets 12F and 12B become less prone to be detached from each other. In this embodiment, the resilient and elastic members may exist only on the both sides in the width direction, or the resilient and elastic members may straddle the inner body 200 in the width direction from one to the other sides of the inner body 200, and be cut off at the central portion that overlaps the inner body 200 in the width direction so as to exert no elastic force (this is virtually equal to no provision of the resilient and elastic members). Further, some or all of the first, second, and third elongated resilient and elastic members 15, 16, and 19 may also straddle the inner body 200 in the width direction from one to the other sides of the inner body 200 so that elastic forces can act entirely on the back side main portion 13 and the back side extended portion 14 in the width direction.

(Inner Body)

The inner body 200 may have any shape, and is of a rectangle in the illustrated arrangement. As shown in FIG. 3, the inner body 200 includes a face sheet 30 facing the body of a wearer, a liquid impervious sheet 11, and an absorbent structure 50 interposed between the two sheets. A crotch outer sheet 12M may be fixed to the underside of the liquid impervious sheet 11 so as to cover the entire underside of the inner body 200 or cover an entire portion of the inner body 200 exposed between the ventral side outer sheet 12F and the back side outer sheet 12B. In addition, the inner body 200 may have an intermediate sheet (second sheet) interposed between the face sheet 30 and the absorbent structure 50 to quickly transfer a liquid having passed through the face sheet 30 to the absorbent structure 50. However, for prevention of interference with heat transfer to the skin of a wearer, the inner body 200 preferably has no member between the face sheet 30 and the absorbent structure 50, at least in a part of the inner body 200 overlapping a part of the inner body 200 having a high absorbent polymer described later, preferably in the entire inner body 200. Further, in order to prevent leakage of excretion to the both sides of the inner body 200, barrier cuffs 60 and 61 may be erected toward the body of the wearer on the both sides of the inner body 200. Although not shown, constituent members of the inner body 200 can be fixed as appropriate to each other by solid, bead or spiral application of a hot-melt adhesive or the like. In addition, the inner body 200 may be detachably connected to the outer sheets 12F and 12B using mechanical fasteners or adhesive materials.

(Face Sheet)

The face sheet 30 has a liquid pervious property. Therefore, a material for the face sheet 30 may be a porous or nonporous nonwoven fabric or a porous plastic sheet, for example. In addition, there is no particular limitation on raw fibers for use in such a nonwoven fabric. For example, the raw fibers may be any of synthetic fibers based on olefin such as polyethylene or polypropylene, polyester, polyamide or the like, recycled fibers such as rayon or cupra, natural fibers such as cotton or the like, mixed or composite fibers of two or more of the foregoing fibers. Further, the nonwoven fabric may be produced by any processing method. For example, the processing method may be any of known methods such as a spun lace method, spun bonding method, SMS method, thermal bonding method, melt-blown method, needle punching method, air-through method, point bonding method, and the like. In particular, to allow a temperature change to be easily perceived from the face side, nonwoven fabrics processed by the spun-bonding method and the SMS method are preferred for balanced thinness and strength, and nonwoven fabrics processed by the air-through method are preferred for achieving rapid absorption and a dry feel with a low basis weight.

In addition, the face sheet 30 may be a single sheet or a layered sheet obtained by sticking two or more sheets to each other. Similarly, the face sheet 30 may be a single sheet or two or more sheets stuck to each other in a planar direction.

If the face sheet 30 is formed from nonwoven fabric, the nonwoven fabric preferably has a thickness of about 0.1 to 3 mm, in particular 0.5 mm or less, and a basis weight of about 10 to 40 g/m$^2$, in particular 25 g/m$^2$, for excellent heat transfer from the backside to the skin of a wearer.

If the barrier cuffs 60 and 61 are arranged, it is preferred that the both side portions of the face sheet 30 extend to the underside of the absorbent structure 50 between the liquid impervious sheet 11 and the barrier cuffs 60 and 61, and are attached to the liquid impervious sheet 11 and the barrier cuffs 60 and 61 with a hot-melt adhesive or the like for prevention of liquid infiltration. This brings about an advantage that the inner body 200 can be improved in stiffness at the both side portions (Liquid Impervious Sheet)

There is no particular limitation on a material for the liquid impervious sheet 11. For example, the material may be any of film material (water-proof film) of olefin resins such as polyethylene and polypropylene, a layered nonwoven fabric in which a nonwoven fabric is layered on a polyethylene sheet or the like, and a nonwoven fabric in which a water-proof film is interposed for virtual liquid imperviousness (in this case, the water-proof film and the nonwoven fabric constitute a liquid impervious sheet). As a matter of course, in addition to the foregoing examples, there are liquid impervious, moisture pervious sheets that have been favorably used in recent years from the viewpoint of prevention of stuffiness. Such a sheet made of a liquid impervious and moisture pervious material may be a microporous sheet obtained by melting and kneading an inorganic filling agent into an olefin resin such as polyethylene or polypropylene to thereby form a sheet and then extending the sheet in a uniaxial or biaxial direction, for example. Further, the liquid impervious sheet 11 may use a sheet that is given liquid imperviousness without the use of a water-proof film, by using a nonwoven fabric of micro denier fibers, applying heat or pressure to make gaps in fibers smaller with enhanced leakage resistance, coating with high water-absorption resin or hydrophobic resin, or applying a water repellent agent. In addition, from the viewpoint of heat insulation, nonporous films and microporous sheets are preferred for relatively lower air permeability.

For an enhanced leakage preventing property, the liquid impervious sheet 11 preferably wraps around the both sides of the absorbent structure 50 and extends to the both side portions of the absorbent structure 50 on the face sheet 30 side. This also improves stiffness of the inner body 200 at the both side portions. An appropriate width of the extended portion is about 5 to 20 mm on both of the right and left sides. In the illustrated example, all of the top sheet 11, the back sheet 12, and a barrier sheet 62 wrap around the absorbent body. Alternatively, the back sheet 12 alone may wrap around the absorbent body 13 or none of the sheets may wrap around the absorbent body 13. If the back sheet 12 alone wraps around the absorbent body, the top sheet 11 and the barrier sheet 62 form side flaps together with the outer sheet 20. In this case, the outer sheet 20 has a liquid impervious property, or another liquid impervious sheet is interposed between the outer sheet 20 and the back sheet 12 (this liquid impervious sheet preferably has a square shape or a shape of a sand clock so as to cover the face sheet). In addition, if the back sheet 12 also does not wrap around the absorbent body, another liquid impervious covering sheet, in place of the back sheet 12, extends from the backside to the face side of the absorbent body side portions and is fixed at both sides thereof.

The liquid impervious sheet 11 may also have designed patterns prepared by printing or coloring on the inner or outer surface. In addition, the liquid impervious sheet 11 may have a printed or colored design sheet attached to the outer surface, as a member different from the crotch outer sheet 12M. Further, the liquid impervious sheet 11 may have inside an excretion indicator 80 that changes in color when absorbing a liquid. In addition, reference numeral 90 denotes a disposal tape for fastening a rolled diaper after use.

(Barrier Cuffs)

Barrier cuffs 60 and 61 are band-like members that extend in the entire front-back direction along the both sides of the inner body 200. The barrier cuffs 60 and 61 are provided to block urine or loose stool moving laterally over the face sheet 30 and to prevent lateral leakage.

In this embodiment, double barrier cuffs 60 and 61 are disposed on each of the right and left sides of the inner body 200, as shown in FIGS. 3 and 4. In the open diaper, as shown in the drawings, the inner barrier cuffs 61 are diagonally erected from the side portions toward the central portion of the inner body 200 in the width direction. The outer barrier cuffs 60 are erected from the side portions of the inner body 200 on the outer side of the inner barrier cuffs 61 in the width direction, root sections thereof are diagonally erected toward the central portion of the inner body 200 in the width direction, and central to leading end portions thereof are diagonally erected outward in the width direction.

More specifically, the inner barrier cuffs 61 are each configured in such a manner that a band-like barrier sheet 62 being the same in length as the inner body 200 in the front-back direction, is folded back and doubled in the width direction, and a plurality of elongated resilient and elastic members 63 is fixed in an extended state in the longitudinal direction on folded sections and surrounding sections of the doubled sheet at intervals therebetween in the width direction. The elongated resilient and elastic members 63 are not fixed at front and rear ends to the barrier sheet 62, and are fixed at the intermediate portion to the barrier sheet 62 in such a manner that the barrier cuffs can extend and contract in the front-back direction. The barrier sheet 62 may use favorably a soft nonwoven fabric with excellent uniformity and concealment properties such as spun-bonded nonwoven fabrics (SS, SSS, and the like), SMS nonwoven fabrics (SMS, SSMMS, and the like), or melt-blown nonwoven fabrics, which are made water-repellent as required using silicon or the like. A basis weight of fibers in the fabric is preferably about 10 to 30 g/m$^2$. In particular, if the temperature changing substance is disposed at the side portions, it is preferred to use a nonwoven fabric lower in basis weight and higher in air permeability to thereby allow a wearer to sense easily a temperature change from the side portions and prevent stuffiness in the diaper. The elongated resilient and elastic members 63 may use rubber threads or the like. If spandex rubber threads are used, a fineness thereof is preferably 420 to 1,120 dtex, more preferably 620 to 940 dtex. The spandex rubber threads are preferably fixed at an extension ratio of preferably 150 to 350%, more preferably 200 to 300%. In addition, although not shown, a water-proof film may be interposed in the two-fold barrier sheet.

Preferably, the inner barrier cuffs 61 each have one or two elongated resilient and elastic members 63 at the leading end thereof, and more preferably, the inner barrier cuffs 61 have each also one or two elongated resilient and elastic members 63 at an intermediate portion between the leading end and base end portions. With the elongated resilient and elastic members 63 as supporting points at the intermediate portions, the inner barrier cuffs 61 are prone to contact by surface the skin of the wearer smoothly in an area ranging from the intermediate to leading end portions. The inner barrier cuffs 61 have preferably the elongated resilient and elastic members 63 disposed at the intermediate portions in a range corresponding to 30 to 70% of height of the inner barrier cuffs 61 (the length of the projecting section in the width direction). In disposable diapers for babies and infants, the preferred height of the inner barrier cuffs 61 is about 15 to 35 mm, and therefore the inner barrier cuffs 61 each have preferably the elongated resilient and elastic members 63 disposed in an area ranging from the leading end portion toward the base end portion by 5 to 25 mm, more preferably by 12 to 18 mm. If the elongated resilient and elastic members 63 are disposed in parallel at the leading end and/or intermediate portions of the inner barrier cuffs 61, an interval 61*d* therebetween is preferably 2 to 10 mm, more preferably 2 to 6 mm.

In each of the inner barrier cuffs 61, an end of a portion on an opposite side of the folded section in the width direction is designated as an attachment section (inner attachment section) 65 that is fixed on the side portions of the inner body 200 from the top to underside surfaces; a section other than the attachment section 65 is designated as a projecting section 66 (which is located on the folded-back section and constitutes an inner projecting section) that is projecting from the attachment section 65; both ends of the projecting section 66 in the front-back direction are fixed to the surface of the face sheet by a front-back fixed portion 67 with the use of a hot-melt adhesive or heat sealing; an intermediate portion in the front-back direction is designated as a non-fixed free portion (inner free portion); and the elongated resilient and elastic members 63 are fixed in an extended state to the free portion in the front-back direction.

The outer barrier cuffs 60 each are basically identical in structure to the inner barrier cuffs 61, except that: an attachment section (outer attachment section) 68 is fixed to an external surface of the inner barrier cuff 61, nearer the central portion of the inner body 200 on the underside in the width direction than the attachment section 65 of the inner barrier cuff 61; both ends of a projecting section (outer projecting section) 69 in the front-back direction include a root section that passes by the side portion of the inner body 200 from the attachment section 68, extends to the surface of both ends of the inner projecting section 66 of the inner barrier cuff 61 in the front-back direction and is fixed to the surface of the both ends of the inner projecting section 66 in the front-back direction, and include a leading end portion that is folded back from a leading end of the root section outward in the width direction and is fixed to the root section; and layout and number of the elongated resilient and elastic members 63 are different from those in the inner barrier cuffs 61.

However, similarly to the outer barrier cuffs 61, the inner barrier cuffs 61 each may also be configured in such a manner that a leading end of the inner projecting section is folded back outward in the width direction, more specifically, the leading end is folded back outward in the width direction and fixed to the root section, provided that the leading end thereof is situated at ½ or less, preferably ⅓ of less of the height of the inner barrier cuffs 61 (the length of the projecting section in the width direction).

The number of the elongated resilient and elastic members 63 is preferably 2 to 6, more preferably 3 to 5, at each of free portions (outer free portions) of the outer barrier cuffs 60. The interval 60*d* therebetween is appropriately set between 3 to 10 mm. In such an arrangement, the outer barrier cuffs 60 are likely to contact by surface the skin of the wearer in areas with the elongated resilient and elastic members 63. The outer barrier cuffs 60 may also have the elongated resilient and elastic members 63 at the root sections as well as the leading end portions. A fineness and extension ratio of the elongated resilient and elastic members 63 on the outer barrier cuffs 61 may be the same as those on the inner barrier cuffs 61. Preferably, a fineness of the elongated resilient and elastic members 63 on the outer barrier cuffs 61 is identical to or more larger than those on the inner barrier cuffs 61, and an extension ratio of the elongated resilient and elastic members 63 on the outer barrier cuffs 61 is identical to or lower than those on the inner barrier cuffs 61.

In addition, it is preferred that a front-back direction length L6 of the front-back fixed portions 67 of the projecting sections 66 and 69 in the inner barrier cuff 61 is equal to or smaller than that in the outer barrier cuff 60. It is also preferred that a front-back direction fixing length of the elongated resilient and elastic members 63 in the inner barrier cuff 61 is equal to or larger than that in the outer barrier cuff 60. Boundaries between the attachment section 65 and the projecting section 66 may be identically located in the inner barrier cuff 61 and the outer barrier cuff 60, but preferably, the boundary in the outer barrier cuff 60 is located nearer the central portion of the inner body 200 in the width direction than the boundary in the inner barrier cuff 61. In this case, a separation distance between the boundaries is preferably 10 mm or less.

Preferably, the outer barrier cuffs 60 and the inner barrier cuffs 61 each have linear root fixed portions formed with a hot-melt adhesive or by heat sealing, at edges of the attachment sections 68 and 65 facing the projecting sections 66 and 69, respectively. In addition, other fixed portions can be fixed in appropriate patterns with a hot-melt adhesive or the like. The linear root fixed portions are positioned preferably on the top side of the inner body 200 in the vicinities of the side portions (specifically, at a position of 0 to 5 mm, preferably 0 to 3 mm, from the side edge of the inner body 200 in the width direction) or on the underside of the inner body 200. In this case, since the outer barrier cuffs 60 and the inner barrier cuffs 61 are each folded back and fixed on the top side virtually only at the both front-back ends, the barrier cuffs are erected outward in the width direction at the crotch portion which is not sufficiently affected by an action of the front-back fixed portions 67 toward the central portion of the inner body 200 in the width direction, whereby wide pockets can be formed by the inner barrier cuffs 61. If the linear root fixed portions are situated on the top side at positions of 5 mm or more from the side edges of the inner body 200 in the width direction, the barrier cuffs are erected at the crotch portion toward the central portion of the inner body 200 in the width direction, whereby narrower pockets are undesirably formed by the inner barrier cuffs 61. If the root fixed portions are to be provided on the underside, the root fixed portions are appropriately situated at positions of 0 to 20 mm from the side edges of the inner body 200, or may be situated at positions in the excess of 20 mm.

The attachment sections 68 and 65 of the outer and inner barrier cuffs 60 and 61 may be fixed to appropriate members of the inner body 200, such as the face sheet 30, the liquid impervious sheet 11, the absorbent structure 50, or the like. In addition, either of the barrier cuffs may be fixed to the inner body 200 via the other barrier cuff.

In the thus configured outer and inner barrier cuffs 60 and 61, contraction forces of the elongated resilient and elastic members 63 act so as to bring the both front-back ends of the barrier cuffs closer to each other. However, the both front-back ends of the projecting sections 66 and 69 are fixed so as not to erect, whereas portions between the both ends are not fixed as free portions. Accordingly, the outer and inner barrier cuffs 60 and 61 are erected such that only the free portions contact the skin of the wearer as shown in FIG. 3. In particular, with the attachment sections 68 and 65 located on the underside of the inner body 200, the outer and inner barrier cuffs 60 and 61 are erected so as to open outward in the width direction at the crotch portion and a surrounding portion thereof, and therefore the outer and inner barrier cuffs 60 and 61 contact by area the legs of the wearer, thereby resulting in an increased fit. Meanwhile, on the both front and back sides (ventral and back sides) of the crotch portion, the outer and inner barrier cuffs 60 and 61 are restricted by the front-back fixed portions 67 so as not to open outward in the width direction, and therefore the inner barrier cuffs 61 and the lower half portions of the outer barrier cuffs 60 are erected high. This prevents leakage from the both sides of the inner body 200 at the ventral and back portions in a reliable manner. In addition, the front-back fixed portions 67 of the projecting sections 66 in the inner barrier cuffs 61 are not folded back, and the front-back fixed portions 67 of the projecting sections 68 in the outer barrier cuffs 60 are folded back outward. Accordingly, separation of the inner and outer free portions in the outer and inner barrier cuffs 60 and 61 is maintained. As a result, the outer and inner barrier cuffs 60 and 61 are erected reliably at wide intervals, and are fitted individually to the legs of the wearer, thereby providing an excellent leakage preventing property.

The dimensions of the barrier cuffs 60 and 61 can be decided as appropriate. In disposable diapers for babies and infants, as shown in FIG. 7 for example, an erection height W5 of the inner barrier cuff 61 (a length of the projecting section 66 in the width direction in the open diaper) is 10 to 50 mm, in particular preferably 15 to 35 mm. An erection height W6 of the outer barrier cuff 60 (a length of the projecting section 69 in the width direction of the open diaper) is preferably 15 to 60 mm, in particular preferably 20 to 40 mm. In addition, when the inner barrier cuffs 61 are folded toward the top surface of the face sheet 30, a separation distance W4 between the leading ends of the inner barrier cuffs 61 is preferably 60 to 170 mm, in particular preferably 70 to 120 mm. In addition, when the outer barrier cuffs 60 are flatly folded in parallel to the top surface of the face sheet 30, a separation distance W3 between folding lines located at innermost positions in the outer barrier cuffs 60 is preferably 60 to 190 mm, in particular preferably 70 to 140 mm.

Alternatively, only either of the outer and inner barrier cuffs 60 and 61 may be provided, unlike the illustrated embodiment.

(Absorbent Structure)

The absorbent structure 50 has the absorbent body 56, and an absorbent body covering sheet 58 that covers the entire absorbent body 56. The covering sheet 58 may be omitted.

(Absorbent Body)

The absorbent body 56 can be formed by a fiber aggregate. Such a fiber aggregate may use accumulated short fibers such as fluff pulp, synthetic fibers or the like, or may use a filament aggregate that can be obtained by opening as necessary a tow (fiber bundle) of synthetic fibers constituted by cellulose acetate or the like. From the viewpoint of a liquid retention property, hydrophilic fibers or hydrophilically-processed fibers are preferred. A basis weight of fibers may be about 100 to 300 $g/m^2$ for accumulated fluff pulp or short fibers, for example, and may be about 30 to 120 $g/m^2$ for a filament aggregate, for example. A fineness of synthetic fibers is 1 to 16 dtex, preferably 1 to 10 dtex, more preferably 1 to 5 dtex, for example. If a filament aggregate is used, filaments may be non-crimped fibers but preferably are crimped fibers. A degree of crimping of the crimped fibers may be about 5 to 75 crimps per inch, preferably about 10 to 50 crimps per inch, and more preferably about 15 to 50 crimps per inch, for example. In many cases, uniformly crimped fibers are used. Preferably, the absorbent body 56 has high-absorbent polymer particles dispersed and retained therein.

The absorbent body 56 may be rectangular. However, as shown in FIG. 6, the absorbent body 56 is preferably formed in the shape of a sand clock, including: a front end portion 56F; a back end portion 56B; and a narrower portion 56N that is located between the front and back end portions 56F and 56B and is narrower than the same, thereby to improve the absorbent body 56 itself and the barrier cuffs 60 and 61 in fit property around the legs. Assuming that a front-back direction length of the absorbent body front end portion 56F is designated as L1; a front-back direction length of an overlap between the absorbent body 56 and the ventral side outer sheet 12F is designated as L2; a front-back direction length of the absorbent body back end portion 56B is designated as L3; a front-back direction length of an overlap between the absorbent body 56 and the back side outer sheet 12B is designated as L4; a minimum width of the narrower portion 56N is designated as W1; and widths of the absorbent body front end portion 56F and absorbent body back end portion 56B are designated as W2, the absorbent body 56 is preferably configured so as to satisfy Equations (1) to (4) listed below.

$$70 \text{ mm} \leq W1 < W2 \leq 190 \text{ mm} \quad (1)$$

$$0.5 \leq W1/W2 \leq 0.85 \quad (2)$$

$$0 \text{ mm} \leq L1 - L2 \leq 70 \text{ mm} \quad (3)$$

$$0 \text{ mm} \leq L3 - L4 \leq 50 \text{ mm} \quad (4)$$

If W1 and W2 are too narrow, the barrier cuffs 60 and 61 are unstably erected and the absorbent body is unsatisfactorily improved in absorption capacity. If W1 and W2 are too wide, the absorbent body is decreased in a fit property and therefore deteriorates wear comfort.

In addition, when the absorbent body 56 falls within the foregoing value ranges, the absorbent body 56 does not exist at the crotch portion in the vicinities of the attachment sections 65 of the barrier cuffs 60 and 61. Accordingly, the barrier cuffs 60 and 61 increase in the degree of freedom of movement. As a result, the barrier cuffs 60 and 61 become likely to open outward in the width direction and contact by area the skin of the wearer, whereby the movements of the legs of the wearer can be more suitably followed by the fitting surfaces of the barrier cuffs 60 and 61. Since the absorbent body 56 exists in sufficient areas of the inner body 200 on the both sides at the front and back side portions, the barrier cuffs 60 and 61 are stably erected with the absorbent body 56 as a base point (supporting point). An area of the diaper ranging from the front and back sides to the crotch portion constitutes a displacement section where the barrier cuffs 60 and 61 shift from an erected posture to an opening posture outward in the width direction with respect to the both side edges of the inner body 200 in the width direction. This posture shift of the barrier cuffs 60 and 61 is supported by the absorbent body 56 existing on the side portions of the inner body 200, whereby the barrier cuffs 60 and 61 are entirely erected in a stable manner. If the absorbent body 56 falls outside the foregoing value rages and the narrower portion is too large, the barrier cuffs 60 and 61 are excessively increased in the degree of the freedom of movement at the crotch portion, and may be likely to create a gap between the leg portions of the diaper and the legs of the wearer. In addition, the barrier cuffs 60 and 61 may be erected unstably without a base point (supporting point) at the crotch portion on the front and back sides. In contrast, if the narrower portion is too small, the barrier cuffs 60 and 61 are undesirably decreased in the degree of the freedom of movement.

Further, the front-back direction length L7 of the entire narrower portion 56N is preferably 80 mm or more, in particular preferably 120 to 260 mm. If the front-back direction length L7 of the narrower portion 56N is too short, the barrier cuffs 60 and 61 are undesirably decreased in the degree of the freedom of movement, and the absorbent body 56 decreases a fit to the legs of the wearer and interferes with the movements of the legs. If the length L7 is too long, the barrier cuffs 60 and 61 cannot be stably erected.

(High-Absorbent Polymer Particles)

The high-absorbent polymer particles may be not only "particles" but also "powders". A particle diameter of the high-absorbent polymer particles may be the same as that of particles used in this kind of absorbent articles, and is 1,000 μm or less, desirably in particular 150 to 400 μm. There are no particular limits on a material for the high-absorbent polymer particles, and a preferred material is 40 g/g or more in capacity of water absorption. The high-absorbent polymer particles may be based on starch, cellulose or synthetic polymer, and may use starch-acrylic acid (salt) graft copolymer, saponified product of starch-acrylonitrile copolymer, cross-linked sodium carboxymethyl cellulose, acrylic acid (salt) polymer, or the like. A shape of the high-absorbent polymer particles is preferably a commonly used particulate shape, and may also be any other shape.

The high absorbent polymer may be combined with an antibacterial substance. In particular, preferred high-absorbent polymer particles are antibacterial and deodorant high-absorbent polymer particles that contain zeolite particles in which some or all of ion-exchangeable ions are substituted by silver ions (hereinafter referred to as antibacterial and deodorant zeolite) or antibacterial and deodorant high-absorbent polymer particles in which antibacterial and deodorant zeolite particles are attached by static electricity to surfaces of high-absorbent polymer particles.

The high-absorbent polymer particles preferably deliver a water absorption speed of 40 seconds or less. If the water absorption speed exceeds 40 seconds, a backflow phenomenon becomes prone to occur, where a liquid having been supplied to the absorbent body 56 flows back out of the absorbent body 56.

In addition, the high-absorbent polymer particles are preferably 1,000 Pa or more in gel strength. This prevents effectively a sticky feel after absorption of a liquid even if the absorbent body 56 is high in bulk.

A basis weight of the high-absorbent polymer particles may be 50 to 800 $g/m^2$, in particular preferably 100 to 40 $g/m^2$. If the basis weight of the polymers is less than 50 $g/m^2$, it is difficult to ensure a sufficient absorption capacity. If the basis weight exceeds 800 $g/m^2$, the high-absorbent polymer particles become saturated in effectiveness.

If necessary, the high-absorbent polymer particles can be adjusted in density or amount of dispersion in the planar direction of the absorbent body 56. For example, an amount of dispersion may be made larger at a liquid excreted portion than other portions. With regard to a difference between the sexes, the dispersion density (amount) may be increased at the front side portion for men or increased at the middle portion for women. The polymer may not exist locally (for example, in spots) in the absorbent body 56 along the planar direction.

In particular, the high absorbent polymer preferably has a water absorption speed of 50 seconds or less for retaining urine changed in temperature by a temperature changing substance described later at a position nearer the skin of a wearer. With a low water absorption speed, most of urine with a temperature change is not absorbed but passed to the backside of the sheet.

If the absorbent body 56 is covered with one absorbent body covering sheet, the seam of the absorbent body covering sheet 58 on the side facing the skin of a wearer, has preferably an overlapping width 58W of 40 mm or less, in particular 20 mm or less, which is smaller than a width 40W of a region having the temperature changing substance, so as to allow the wearer to perceive a temperature change in an effective way. In addition, in another preferred embodiment, the seam of the absorbent body covering sheet 58 is laterally shifted so as to avoid the central portion in the width direction contacting a point of urination. In particular, it is preferred that the sheet overlapping section in the seam of the absorbent body covering sheet 58 on the side facing the body of a wearer does not overlap a temperature changing substance welded section 40 described later.

(Absorbent Body Covering Sheet)

The absorbent body covering sheet 58 may use any of tissue paper, crepe paper, nonwoven fabrics, polyethylene laminated nonwoven fabrics, foraminous sheets, and the like. The absorbent body covering sheet 58 desirably is a finely woven sheet so as not to let the high-absorbent polymer particles (and the temperature changing substance if the same is provided within the absorbent body covering sheet) pass through. In addition, the absorbent body covering sheet 58 is appropriately thin and has a low basis weight to allow a wearer to sense easily a temperature change from a face side. The absorbent body covering sheet 58 preferably has a thickness of about 0.05 to 3 mm, in particularly 0.2 mm or less, and a basis weight of about 5 to 25 g/m$^2$, in particular 15 g/m$^2$ or less, for excellent heat transfer performance from a back side to the skin of a wearer. If any nonwoven fabric is used for the absorbent body covering sheet 58, nonwoven fabrics processed by a spun-bonding method and an SMS method, in particular, nonwoven fabrics processed by an SMS method, are preferred for balanced thinness and strength. Materials for such nonwoven fabrics may use polypropylene or polyethylene/polypropylene.

(Crotch Outer Sheet)

The crotch outer sheet 12M is provided on the under surface of the inner body 200 and exposed to the external surface of the product. A material for the crotch outer sheet 12M may be the same as those for the ventral side outer sheet 12F and the back side outer sheet 12B, or may be one having higher strength or a deodorant differently from those for the ventral side outer sheet 12F and the back side outer sheet 12B. More specifically, the material may be any of various nonwoven fabrics such as spun-bonded nonwoven fabric, melt-blown nonwoven fabric, point-bonded nonwoven fabric, air-through nonwoven fabric, air-point nonwoven fabric, spun-lace nonwoven fabric, and SMS nonwoven fabric, which are formed by fibers of, for example, PP, PP/PE, or PP/PET, or any of the foregoing nonwoven fabrics to which a deodorant or the like is added.

When a wearer is in a sitting position, a high body pressure is applied to the crotch outer sheet 12M. Accordingly, the crotch outer sheet 12M is preferably constituted by a material with high fastness to rubbing (causing no fluff).

The crotch outer sheet 12M may include some design elements prepared by printing or coloring. In combination with the above-mentioned design sheet, the crotch outer sheet 12M and the design sheet are preferably arranged such that the design matters on the two sheets do not overlap.

The crotch outer sheet 12M preferably uses a resilient and elastic nonwoven fabric which is extended and attached in a longitudinal direction of the inner body 200, thereby increasing a fit at the crotch portion.

When the crotch outer sheet 12M extends from the side portions to the body sides in the width direction and are attached and fixed with a hot-melt adhesive or the like to the external surface of the barrier sheet 62, the stiffness of the inner body 200 can be improved at the both side portions. In such an arrangement, the crotch outer sheet 12M uses preferably a high-stiffness (high-firmness) sheet. More specifically, the crotch outer sheet 12M may use a sheet in which a sum of values of bending resistance in MD and CD directions of the sheet measured by Clark process (JIS L1096C) is 100 mm or more, preferably 150 mm or more.

In the illustrated example, the crotch outer sheet 12M is sandwiched between the inner body 200 and the ventral side and back side outer sheets 12F, 12B at sections in which the ventral side and back side outer sheets 12F, 12B and the inner body 200 overlap each other. Alternatively, the crotch outer sheet 12M may be attached to outside the ventral side and back side outer sheets 12F, 12B. The crotch outer sheet 12M is attached to the under surface of the inner body 200 and the inner surfaces or outer surfaces of the ventral side and back side outer sheets 12F and 12B with a hot-melt adhesive or the like.

<Features>

The present invention is based on an idea that urine is cooled or heated by a temperature changing substance 40 at a region close to the skin of a wearer, and then is absorbed and retained by the high absorbent polymer. In one preferred embodiment of the present invention, for example, as shown in FIG. 3 and others, the temperature changing substance for cooling or heating urine by contact with the urine, is disposed on a surface of the absorbent body 56 containing the high absorbent polymer at least in a face side layer within the absorbent body covering sheet 58 of the absorbent structure 50.

The temperature changing substance 40 is intended to cool or heat urine by contact with the urine to absorb or release heat of dissolution, heat of hydration, heat of reaction, or the like. Examples of the temperature changing substance 40 absorbing heat by dissolution in urine, include: hydrate salts such as sodium acetate, sodium carbonate, sodium sulfate, sodium thiosulfate, and sodium phosphate; anhydrous salts such as ammonium nitrate, potassium nitrate, ammonium chloride, potassium chloride, and sodium nitrate; urea; and sugar alcohols such as xylitol and sorbitol. Examples of the temperature changing substance 40 releasing heat by dissolution in urine include aluminum chloride, aluminum sulfide, aluminum potassium sulfate, and the like. Out of the foregoing substances, the present invention can preferably uses sugar alcohols such as sorbitol and xylitol or organic compounds such as urea exhibiting an endothermic effect. In particular, sorbitol and xylitol are preferred because these substances are extremely excellent in solubility, chemically stable, and do not exert any harmful influence on the human body. If a temperature changing substance for absorbing or releasing heat by dissolution in urine is low in solubility in urine, the substance cannot generate a sufficient temperature change. Accordingly, the temperature changing substance preferably has a solubility of 30 g or more, in particular 50 g or more in water of 100 ml at a temperature of 20° C. In addition, the temperature changing substance preferably generates a temperature change of 20 cal/g or more, more preferably 35 cal/g or more.

Examples of the substance absorbing or releasing heat by reaction with urine, include ortho esters, ketals such as a menthone ketal obtained by reacting menthone with an alcohol with a carbon number of 1 to 8 or a polyol with a carbon number of 2 to 8, and structural or optical isomers of the foregoing substances. In addition, examples of the temperature changing substance 40 absorbing or releasing heat by swelling in urine, include a polyacrylic acid lightly cross-linked and partially neutralized.

The temperature changing substance 40 is preferably in particle form (including powder form), but may be in fibrous form or any other form. With nearly equal particle sizes, the particulate temperature changing substance 40 becomes larger in surface area and higher in urine contact efficiency with a lower bulk density, resulting in a higher temperature change speed. This tendency is particularly prominent in the case where the temperature changing substance 40 generates a temperature change by dissolution in urine. The particulate temperature changing substance 40 with a low bulk density is preferably porous particles such as granules, particles with a large number of surface asperities, and particles with fine pores on surface or inside. A bulk density of the particles may be decided as appropriate, but is preferably 50% or less of a real density of the same (having a gap (space) of 50% or more of an apparent volume of the same). For example, sorbitol has a real density of 1.50 g/cm$^3$, and therefore a preferred bulk density of the same is 0.75 g/cm$^3$ or less, more preferably 0.50 to 0.70 g/cm$^3$, in particular preferably 0.55 to 0.65 g/cm$^3$. In addition, particles with a large size are low in apparent bulk density and also are not large in surface area. Accordingly, the particulate temperature changing substance 40 preferably has an average particle size of 200 to 600 μm (JIS K 1474-2007, median diameter).

In addition, the high absorbent polymer for absorbing and retaining cooled or heated urine may be identical to that contained in the absorbent body 56 described above, and in particular preferably has a water absorption speed of 50 seconds or less. With a low water absorption speed, most of cooled or heated urine is not absorbed but passed to the backside of the sheet.

The embodiment in which the temperature changing substance for cooling or heating urine by contact with the urine is arranged on the surface of the absorbent body 56, as shown in FIG. 3, can be manufactured, for example, by forming the absorbent body 56 containing the high-absorbent polymer particles along a virtually entire thickness direction thereof and then sprinkling or projecting the particulate temperature changing substance 40 onto the surface of the absorbent body 56. In particular, by projecting the particulate temperature changing substance 40, part of the temperature changing substance 40 enters the absorbent body 56, and therefore the absorbent body 56 contains on the face side layer a mixture of the temperature changing substance 40 and the high absorbent polymer and a layer containing virtually only the temperature changing substance 40 on the face side layer. In such form, the particle layers of the absorbent body 56 can be preferably thin to thereby hardly cause a granular, discomfort feeling to a wearer. Alternatively, to allow a wearer to sense more strongly a temperature change immediately after urination, almost all the temperature changing substance 40 may be disposed on the upper side of the absorbent body 56 without forming the mixture layer.

In other words, out of the high-absorbent polymer particles generally contained in the absorbent body 56, this embodiment uses the particles resided in the face side layer to absorb and retain cooled or heated urine. Therefore, in this embodiment, when the density of the high absorbent polymer is higher on the face side than the back side, the absorbent body 56 preferably can retain more cooled or heated urine in the face side and generate a larger temperature change on the surface of the article. More preferably, when the absorbent body 56 is formed with a density gradient such that the high absorbent polymer becomes gradually higher in density with increasing proximity to the face side of the absorbent body 56 or the high absorbent polymer becomes higher in density in a step-by-step manner with increasing proximity to the face side of the absorbent body 56, the absorbent body 56 is significantly effective in achieving a temperature change on the surface of the article. Such a density gradient can be formed by a high absorbent polymer having a particle size distribution with a high content of large-sized particles that are less prone to enter the absorbent body 56.

In such a configuration, urine having passed through the face sheet 30 and reached the face side of the absorbent body 56, is cooled or heated by the temperature changing substance 40, moved to the backside of the absorbent body 56, and then absorbed by the high absorbent polymer. Accordingly, the temperature of the face side layer of the absorbent body 56 containing the high absorbent polymer is effectively transferred to the surface of the article, thereby to allow a wearer to perceive a temperature change. Preferably in particular, if the temperature changing substance 40 is a soluble material, the temperature changing substance 40 dissolves in urine on urination, and therefore the face side of the absorbent body 56 is exposed so that the temperature of the high absorbent polymer absorbing and retaining the cooled or heated urine can be transferred directly to the surface of the article.

In another preferred embodiment, the absorbent body 56 has on the face side a mixture layer 41 of the temperature changing substance and the high absorbent polymer, as shown in FIG. 10. Such an embodiment can be produced by sprinkling or projecting a mixture of the particulate temperature changing substance and the high-absorbent polymer particle onto the face side of the absorbent body 56, for example. In particular, projecting the temperature changing substance 40 can enter part of the temperature changing substance and high-absorbent polymer particles into the absorbent body 56. Accordingly, the absorbent body 56 contains in the face side layer a mixture of the temperature changing substance and the high absorbent polymer. In such form, the particle layer of the absorbent body 56 becomes thin to thereby hardly cause a granular, discomfort feeling to a wearer. The absorbent body 56 of this embodiment may contain the high-absorbent polymer particles in advance or may not contain the same in advance. If the absorbent body 56 does not contain the high-absorbent polymer particles in advance, the high absorbent polymer can be dispensed into the absorbent body 56 during the manufacturing process at the step of projecting the particle temperature changing substance 40 and the high-absorbent polymer particles. This avoids the manufacturing process from being complicated. As a matter of course, almost all the temperature changing substance 40 and the high absorbent polymer can be placed on the upper side of the absorbent body 56.

In this embodiment, urine having passed through the face sheet 30 and been supplied to the mixture layer 41, is cooled or heated by the temperature changing substance, and immediately absorbed by the high absorbent polymer without transferring heat to any other member. This can achieve a large temperature change on the surface of the article.

Alternatively, if the particulate temperature changing substance 40 and the high-absorbent polymer particles are sprinkled or projected to the face side of the absorbent body 56, the two kinds of particles may be sprinkled or projected separately, not together, so that the two can be virtually layered (including the state where there is a partly mixed layer in the intermediate portion in the thickness direction). Preferably in particular, if the high-absorbent polymer particles is first sprinkled or projected, the temperature changing substance 40 is positioned on the high absorbent polymer. In this case, sprinkling and projecting can be separately performed according to the purpose, in such a manner that the former high-absorbent polymer particles are projected and the latter particulate temperature changing substance 40 is sprinkled.

In the specification of the subject application, the expression "sprinkling" refers to allowing a particulate matter to fall freely, and "projecting" refers to applying a particulate matter at an initial velocity in a more vigorous manner than the case of free-falling. If a plurality of kinds of particulate matters are sprinkled or projected over a plurality of times, all the particulate matters can be "projected" at varied initial velocities, thereby making it possible to control the degree of supporting by the fiber aggregate of the absorbent body 56 and control the mixture proportion of the sprinkled particulate matters. For example, if the particulate temperature changing substance 40 and the high-absorbent polymer particles are separately sprinkled or projected as in the foregoing example, the high-absorbent polymer particles are first projected at a higher initial velocity than that of the particulate temperature changing substance. This makes it possible to allow most of the high-absorbent polymer particles to enter the absorbent body 56, and allow most of the particulate temperature changing substance 40 to form a thick layer within the absorbent structure 50 at a position nearest the face side of the same.

There are conventionally well-known techniques of sprinkling or projecting particles in the manufacture of the absorbent structure, and such techniques can be applied to projecting of the temperature changing substance 40 and the high-absorbent polymer particles in the present invention. For example, there is a known technique of improving a dry feel on a diaper surface by interposing a layer of high-absorbent polymer particles between the upper side of the absorbent body 56 and the absorbent body covering sheet 58 to thereby decrease a return of a liquid from the high-absorbent polymer particles. For manufacture of such an absorbent structure 50, there is a known method in which, in a manufacturing line where a diaper is placed with a top side facing the lower side of the line, particles are sprinkled directly to the absorbent body covering sheet 58 transported inside out, and then absorbent body 56 is placed upside down on the absorbent body covering sheet 58. However, if particles are sprinkled directly to the absorbent body covering sheet 58 in a high-speed manufacturing line, this causes a problem of the particles being airborne. This problem is hard to solve even with intervention of an adhesive. The problem of airborne particles can be solved by employing a forming method of the absorbent structure 50 in which: in the manufacturing process of the absorbent article, the absorbent body 56 is placed on one wide absorbent body covering sheet 58; high-absorbent polymer particles are sprinkled onto the absorbent body 56 and supported on the fiber aggregate (partially within the fiber aggregate) of the absorbent body 56; and then the absorbent body covering sheet 58 extending on the both sides of the backside of the absorbent body 56 is rolled up to wrap the absorbent body 56, thereby to avoid the particles from being airborne in the manufacturing line. In this case, however, the absorbent article 50 has on the surface a seam of the absorbent body covering sheet 58 from which some small-sized high-absorbent polymer particles may slip out before absorbing a liquid. Further, if the face sheet 30 is a loosely woven material for producing a dry feel, some high-absorbent polymer particles may come out from the loose face sheet and be exposed to the side facing the skin of a wearer before or during the use of the diaper. If such a phenomenon takes place, the exposed high-absorbent polymer particles are bulged into jelly-like particle with a recognizably large size after absorption of a liquid. This brings discomfort and unnecessary anxiety to the wearer and a person in charge of diaper replacement. In general, a thin layer of a fiber aggregate or the like is disposed on a layer of particulate matters to thereby prevent the high-absorbent polymer particles from slipping out. Nevertheless, the layer of a fiber aggregate is more prone to cause a return of a liquid than the high absorbent polymer, and therefore is not preferred for improvement of a dry feel.

On the other hand, if the particulate temperature changing substance 40 and the high-absorbent polymer particles are sprinkled or projected, in particular projected, onto the surface of the absorbent body 56, the absorbent structure 50 can be formed in such a manner that: in the manufacturing process of the article, the absorbent body 56 is placed on one wide absorbent body covering sheet 58; the high-absorbent polymer particles and the particulate temperature changing substance 40 are sprinkled or projected onto the absorbent body 56 such that a layer of the particulate temperature changing substance 40 is formed on a layer of the high-absorbent polymer particles, thereby to allow these particulate matters to be supported on the fiber aggregate (partly within the fiber aggregate) of the absorbent body 56; and the absorbent body covering sheet 58 extending on the both sides of the backside of the absorbent body 56 is rolled up to wrap the absorbent body 56. This allows the layer of the temperature changing substance 40 to cover the high-absorbent polymer particles to thereby prevent the high-absorbent polymer particles from slipping out. In this case, the particulate temperature changing substance 40 may slip out and be exposed at the side facing the skin of a wearer. However, if the temperature changing substance 40 of a soluble type is used, the temperature changing substance 40 dissolves and disappears during the use of the diaper, which is less prone to cause the foregoing problem.

Not only in the case where the particulate temperature changing substance 40 and the high-absorbent polymer particles are sprinkled or projected onto the face side of the absorbent body 56, but also in the case where the particulate temperature changing substance 40 is sprinkled or projected onto the face side of the absorbent body 56 containing the high-absorbent polymer particles, the density of the high absorbent polymer can be increased on the upper side of the absorbent body 56 to thereby accomplish the advantage of preventing the high-absorbent polymer particles from slipping out while achieving a dry feel, as described above, since there is no need to provide a thin layer of a fiber aggregate or the like on the upper side of the absorbent body 56.

The seam of the absorbent body covering sheet 58 on the upper side (facing the skin of a wearer) of the absorbent structure 50 as stated above, has preferably an overlapping width 58W of 40 mm or less, in particular 20 mm or less, which is smaller than a width 40W of a region having the temperature changing substance 40, so as to allow a wearer to perceive a temperature change in an effective way. For the foregoing reason, the high-absorbent polymer particles do not slip out even with such a narrow seam. In addition, in another preferred embodiment, the seam of the absorbent body covering sheet 58 is laterally shifted so as to avoid the central portion in the width direction contacting a point of urination.

In another embodiment, as shown in FIG. 11, a temperature changing sheet 42 formed by holding a particulate temperature changing substance with a liquid pervious fiber aggregate sheet of paper, nonwoven fabric, or the like, is attached to the face side of the absorbent body 56. In this case, the temperature changing sheet 42 preferably uses an air-laid nonwoven fabric sheet formed in such a manner that: the particulate temperature changing substance 40 and the high-absorbent polymer particles 43 are sandwiched in a layered or mixed (not shown) state between entire (or partial) fiber aggregate layers 42a and 42b made of thermally welded fibers, pulp, or the like; and these particulate matters are heated and integrated, as shown in the drawing (in the illustrated embodiment, the temperature changing substance 40 constitutes an upper layer and the high-absorbent polymer particles 43 constitutes a lower layer, but this order may be reversed).

To allow the wearer to perceive his/her urination clearly, the face sheet 30 preferably has a temperature change of 4 degrees or more, in particular 5 degrees or more at the face side. Specifically, in the structure of the absorbent article in which the temperature changing substance 40 and the high absorbent polymer are disposed in the upper layer of the absorbent structure 50 and no other member is interposed between the face sheet 30 and the absorbent structure 50, the following conditions are preferably satisfied to achieve such a temperature change:

Material for the liquid pervious face sheet 30: Nonwoven fabric

Thickness of the liquid pervious face sheet 30: 0.1 to 0.5 mm

Basis weight of the liquid pervious face sheet 30: 10 to 40 $g/m^2$

Material for the absorbent body covering sheet 58: Crepe paper or SMS nonwoven fabric Thickness of the absorbent body covering sheet 58: 0.05 to 0.2 mm Basis weight of the absorbent body covering sheet 58: 5 to 25 g/m²

Kind of the temperature changing substance: Causing an endothermic reaction by dissolution in urine to cool the urine Solubility of the temperature changing substance (in water of 100 ml at 20° C.): 30 g or more, in particular 50 g or more Basis weight of the temperature changing substance: 300 to 800 g/m²

Area of the part having the temperature changing substance: 2,500 to 20,000 mm²

Total amount of change in calorific value possibly caused on the absorbent body 56 by the temperature changing substance: 50 cal or more, in particular 150 cal or more Amount of change in calorific value possibly caused in the part having the temperature changing substance per unit area: 1 cal/cm² or more, in particular 2.5 cal/cm² or more Absorption speed of the high absorbent polymer absorbing urine with a temperature change: 50 seconds or less, in particular 40 seconds or less Basis weight of the high absorbent polymer absorbing urine with a temperature change: 50 to 400 g/m²

Area of the part having the high absorbent polymer absorbing urine with a temperature change: 2,500 to 20,000 mm²

In the foregoing embodiment, the absorbent structure 50 contains the temperature changing substance 40 and the high absorbent polymer. As an alternative to this, a temperature changing layer such as the temperature changing sheet 42 containing the temperature changing substance 40 and the high absorbent polymer 43 absorbing and retaining urine cooled or heated by the temperature changing substance 40 can be provided between the face sheet 30 and the absorbent structure 50, as shown in FIG. 12 (the temperature changing layer may not be limited to sheet form and may be a member in another form or a particulate layer containing the particulate temperature changing substance and the high-absorbent polymer particles in a mixed or layered state). In this case, the temperature changing sheet 42 is identical to the aforementioned sheet, and therefore description of the same will be omitted with use of the identical reference numeral. In this embodiment, if there is no other member between the face sheet 30 and the temperature changing sheet 42, the following conditions are preferably satisfied for achieving the aforementioned temperature change:

Material for the liquid pervious face sheet 30: Nonwoven fabric

Thickness of the liquid pervious face sheet 30: 0.1 to 0.5 mm

Basis weight of the liquid pervious face sheet 30: 10 to 40 g/m²

Material for the absorbent body covering sheet 58: Crepe paper or SMS nonwoven fabric Thickness of the absorbent body covering sheet 58: 0.05 to 0.2 mm Basis weight of the absorbent body covering sheet 58: 5 to 25 g/m²

Kind of the temperature changing substance: Causing an endothermic reaction by dissolution in urine to cool the urine Solubility of the temperature changing substance (in water of 100 ml at 20° C.): 30 g or more, in particular 40 g or more Basis weight of the temperature changing substance: 300 to 800 g/m²

Area of a part of the absorbent structure having the temperature changing substance: 2,500 to 20,000 mm²

Total amount of change in calorific value possibly caused on the temperature changing sheet 42 by the temperature changing substance: 50 cal or more, in particular 150 cal or more Amount of change in calorific value possibly caused in the part having the temperature changing substance per unit area: 1 cal/cm² or more, in particular 2.5 cal/cm² or more Absorption speed of the high absorbent polymer absorbing urine with a temperature change: 50 seconds or less, in particular 40 seconds or less Basis weight of the high absorbent polymer absorbing urine with a temperature change: 50 to 400 g/m²

Area of the part having the high absorbent polymer absorbing urine with a temperature change: 2,500 to 20,000 mm²

Meanwhile, in each of the foregoing embodiments, the part having the temperature changing substance 40 (the part having a mixed layer of the temperature changing substance 40 and the high absorbent polymer in the embodiment with the mixed layer, and the part having the temperature changing substance 40 in the temperature changing sheet 42 in the embodiment with the temperature changing sheet 42) can be positioned as appropriate. Preferably, the temperature changing substance 40 is provided in the front-back direction so as to have a front-back direction length 40L of 30 to 250 mm ranging from a position of 0 to 160 mm forward to a position of 0 to 80 mm backward with respect to a central portion in the front-back direction (crotch portion) CL; and is provided in the width direction so as to be symmetric with respect to a central portion in the width-direction (crotch portion) and have a width 40W of 30 to 140 mm.

In addition, preferably, the part having the high absorbent polymer protrudes beyond the part having the temperature changing substance 40 at either the front-back direction sides or the width-direction sides. Accordingly, the high absorbent polymer is allowed to absorb and retain effectively a portion of urine cooled or heated at the part having the temperature changing substance 40 and spreading in the vicinity of the part having the temperature changing substance 40, which brings about a large temperature change in a wide area of the surface of the article. For example, in the embodiment where the entire absorbent body 56 contains the high-absorbent polymer particles, the foregoing structure can be obtained by disposing the temperature changing substance on the inside of the protruding part of the absorbent body 56 at the circumferential edge. The protruding part having the high absorbent polymer has preferably a protruding width 40x of 15 mm or more.

(Experiments for Temperature Change)

Experimental samples were prepared as follows: an underpants type disposable diaper of a structure shown in FIG. 3 (hereinafter, referred also to structure A); an underpants type disposable diaper of a structure shown in FIG. 12 (hereinafter, referred also to structure B); a commercial underpants type disposable diaper containing a temperature changing substance (HUGGIES Pull-Ups TRAINING PANTS Cool Alert (2T-3T size) manufactured by Kimberly-Clark Worldwide, Inc. This product is close to the structure B with the high absorbent polymer excluded from the temperature changing sheet 42); and a reference underpants type disposable diaper (this product is close to the structure B with the temperature changing sheet 42 excluded). For the structure A, samples 1 to 5 were prepared with different basis weights of the temperature changing substance. The major specifications of those samples are as described below.

(Major Specifications of the Samples of the Structure A)

Liquid pervious face sheet 30: Air-through nonwoven fabric made of PE/PP composite fibers with a thickness of 2 mm and a basis weight of 25 g/m$^2$ Absorbent body covering sheet 58: Crepe paper with a thickness of 1 mm and a basis weight of 15 g/m$^2$ Size of the absorbent body 56: Covering an area from a position of 205 mm forward to a position of 190 mm backward with respect to the central portion in the front-back direction, and from a position of 70 mm leftward to a position of 70 mm rightward with respect to the central portion in the width-direction. The area is 55,300 mm$^2$.

Kind of the temperature changing substance 40: Sorbitol ("Sorbit" with heat of solution of −26 cal/g, produced by Towakasei Kogyo Co., Ltd.)

Solubility of the temperature changing substance 40 (in water of 100 ml at 20° C.): 70 g Size of the part having the temperature changing substance 40: Covering a rectangular area from a position of 160 mm forward to a position of 40 mm backward with respect to the central portion in the front-back direction, and from a position of 50 mm leftward to a position of 50 mm rightward with respect to the central portion in the width-direction. The area is 20,000 mm$^2$.

Total amount of change in calorific value possibly caused on the absorbent body by the temperature changing substance 40: 208 cal (in the case with sorbitol of 400 gsm)

Amount of change in calorific value at the part having the temperature changing substance 40 per unit area: 1.04 cal/cm$^2$ (in the case with sorbitol of 400 gsm)

Absorption speed of the high absorbent polymer: 35 seconds

Basis weight of the high absorbent polymer: 150 g/m$^2$ (the polymer is dispersed uniformly in the absorbent body 56 in the thickness direction)

Size of the part having the high absorbent polymer: The entire absorbent body 56

(Major Specifications of the Sample of the Structure B)

Upper layer 42a of the temperature changing sheet 42: Pulp (with a basis weight of 40 g/m$^2$) and PE/PET bicomponent fiber of 1.7 dtex (with a basis weight of 10 g/m$^2$)

Lower layer 42a of the temperature changing sheet 42: Pulp (with a basis weight of 40 g/m$^2$) and PE/PET bicomponent fiber of 1.7 dtex (with a basis weight of 10 g/m$^2$)

Upper-middle layer 42c of the temperature changing sheet 42: The temperature changing substance 40 (with a basis weight of 400 g/m$^2$)

Lower-middle layer 42d of the temperature changing sheet 42: The high absorbent polymer 43 (with a basis weight of 100 g/m$^2$)

Size of the temperature changing sheet 42: Identical to the part having the temperature changing substance in the structure A Size of the part having the temperature changing substance 40 in the temperature changing sheet 42: The entire temperature changing sheet 42

Size of the part having the high absorbent polymer 43 in the temperature changing sheet 42: The entire temperature changing sheet 42

Liquid pervious face sheet 30: Identical to the structure A

Absorbent body covering sheet 58: Identical to the structure A

Size of the absorbent body 56: Identical to the structure A

Kind of the temperature changing substance 40: Identical to the structure A

Solubility of the temperature changing substance 40 (in water of 100 ml at 20° C.): Identical to the structure A Absorption speed of the high absorbent polymer in the absorbent body 56: Identical to the structure A Basis weight of the high absorbent polymer in the absorbent body 56: Identical to the structure A Size of the part having the high absorbent polymer in the absorbent body 56: Identical to the structure A (Experimental Method and Results)

Artificial urine of 50 cc at a temperature of 37° C. was prepared in a beaker. The artificial urine was supplied to the surface of a sample at the front-back-direction center and the central portion in the width-direction from a height of about 15 cm in about three seconds. Then, a temperature of the sample was measured at a portion of front-back-direction center and the central portion in the width-direction with a diameter of 5 cm, with use of a contactless thermometer at predetermined times.

FIG. 13 shows a graph of measurement results. As seen from the graph, the samples 1 to 5 of the structure A and the sample 6 of the structure B in the present invention, were higher in temperature lowering speed and had lower minimum temperatures as compared with the commercial products, and also maintained the minimum temperatures.

<Embodiment with a Layer Containing a Water-Soluble Substance>

In another embodiment, the absorbent body 56 has on the face sheet 30 side the temperature changing layer 44 that contains the temperature changing substance 40 generating by contact with a liquid a temperature change capable of being perceived by the wearer, and has a layer 46 containing a water-soluble substance 45 under the temperature changing layer 44, as shown in FIG. 14. In the illustrated example, the absorbent body 56 covered with the absorbent body covering sheet 58 has on the face sheet 30 side, that is, on the used side, a separate temperature changing member 47 formed by the layer 44 containing the temperature changing substance 40 and the layer 46 containing the water-soluble substance 45, at the center in the width direction of the longitudinal intermediate portion, as shown in an enlarged view in FIG. 15.

The layer 46 containing the water-soluble substance 45 takes advantage of the fact that it takes a certain period of time for the water-soluble substance 45 to dissolve in urine, thereby to allow the urine on first urination to be retained temporarily in the upper layer of the layer 46 containing the water-soluble substance 45. This prevents the urine from being absorbed immediately in the absorbent body 56. Accordingly, the urine sufficiently contacts the temperature changing substance 40 contained in the upper layer to generate an absolute temperature change and allow the wearer to sense the temperature change reliably.

The separate temperature changing member 47 is disposed at the central portion of the absorbent body 56 in the longitudinal direction and the width directions. In particular, the separate temperature changing member 47 is preferably centered in the width direction. In a diaper for male infants, the separate temperature changing member 47 is preferably positioned forward in the longitudinal direction, and in particular, is preferably disposed so as to cover a part where the absorbent body 56 intersects a line linking the lower end portion of the joined sections of the outer sheet 12 on the both right and left sides. In such an arrangement, the separate temperature changing member 47 can be close to a point of urination and be pressed against at any time the body of a wearer by the action of the resilient and elastic members. This allows a wearer to perceive a temperature change in any position. In addition, in a diaper for female infants, the separate temperature changing member 47 is preferably disposed so as to cover the central portion in the longitudinal direction which is close to a point of urination. Accordingly, in a diaper for male and female infants, the separate temperature changing member 47 is preferably disposed so as to cover the part where the absorbent body 56 intersect a line linking the lower end portion of the joined sections of the outer sheet 12 on the both right and left sides, and cover the central portion in the longitudinal direction. Accordingly, much of a liquid can contact the layer containing the temperature changing substance on urination, thereby to generate a temperature change effectively by the temperature changing substance. In addition, this allows a wearer to feel discomfort due to a temperature change at the most sensitive region. Accordingly, the wearer can perceive a temperature change immediately, and a carer of the wearer or the like can also recognize the temperature change earlier.

In this embodiment, the temperature changing substance 40 may be arranged on the disposable diaper 1 in the form of powder and particulate temperature changing substance 40, or the form of a compact of the same, or the form of a sheet-like matter supporting the same. That is, the powder and particulate temperature changing substance 40 may be sprinkled as it is, the temperature changing substance 40 may be dissolved and formed into a flexible sheet, or the temperature changing substance 40 may be supported by a sheet of nonwoven fabric, paper, or the like. In particular, if the temperature changing substance 40 is formed as a sheet-like matter in the last example, the temperature changing substance 40 may be supported on a base material made of a sheet of nonwoven fabric, paper, or the like, by fixing the powder and particulate temperature changing substance 40 to the sheet material; or impregnating the sheet material with a water solution of the temperature changing substance 40 or applying the solution to the sheet material, and then drying the sheet material; or applying the fused temperature changing substance 40 to the sheet material; or interposing a layer of the temperature changing substance 40 in the layered sheet material; or heating the layered sheet material with the temperature changing substance 40 and fixing the temperature changing substance 40.

The temperature changing substance 40 disposed on the upper layer 44 of the separate temperature changing member 47 is preferably a particulate matter. Water-soluble substances are dissolved at speeds in proportion to surface areas thereof. Therefore, particulate substances are dissolved at higher speeds than block-like substances, if those substances are at the same level in solubility. In addition, out of various (fine) particulate substances, granular substances with many gaps in particle structures (or particulate substances with large surface areas due to indefinite shapes or with micro pores) are dissolved at further higher speeds. Accordingly, the temperature changing substance with a high solution rate generates a temperature change quickly. Therefore, the temperature changing substance 40 disposed on the upper layer 44 of the separate temperature changing member 47 is preferably a (fine) particulate matter, in particular a granular matter.

The temperature changing layer 44 may be formed by covering a compact of the temperature changing substance 40 with a base sheet material of nonwoven fabric, paper, or the like, or by sandwiching the compact in the base sheet material of nonwoven fabric, paper, or the like. A basis weight of the temperature changing substance 40 is 50 to 1,000 g/m$^2$, preferably 300 to 700 g/m$^2$. With a basis weight of less than 50 g/m$^2$, the temperature changing substance 40 cannot generate an obvious temperature change to an extent of being perceivable. With a basis weight of more than 1,000 g/m$^2$, the temperature changing substance 40 becomes saturated and causes cost increase.

In addition, the layer 44 containing the temperature changing substance 40 preferably has the high absorbent polymer. Accordingly, the layer 44 containing the temperature changing substance 40 is bulged on absorption of a liquid, and therefore the layer 44 containing the temperature changing substance 40 becomes prone to contact the body of a wearer and allows the wearer to perceive a temperature change reliably. In addition, the liquid with a temperature change does not spread in the absorbent body but is retained by the high absorbent polymer under the action of the temperature changing substance, thereby to maintain the temperature change capable of being perceived by the wearer.

For example, the high absorbent polymer is granular powder and is mixed into the particulate temperature changing substance 40, or mixed into the absorbent body 56 in the vicinity of the layer 44 containing the temperature changing substance 40, or sprinkled onto the layer 44 containing the temperature changing substance 40. The high absorbent polymer may be identical to that contained in the absorbent body 56. In particular, the high absorbent polymer preferably has an absorption speed of 50 seconds or less, more preferably 40 seconds or less, so as to retain much of a liquid with a temperature change before spreading, whereby a beneficial effect of retaining a temperature change can be expected. The absorption speed here refers to a period of time required for a 2-g specimen to absorb a normal saline of 50 g, and is measured in accordance with JIS K 7224-1996. A basis weight of the high absorbent polymer is 20 to 200 g/m$^2$, preferably 50 to 100 g/m$^2$. With a basis weight of less than 20 g/m$^2$, the high absorbent polymer may not bulge sufficiently in the layer 44 containing the temperature changing substance 40 by absorption of a liquid. With a basis weight of more than 200 g/m$^2$, the high absorbent polymer becomes saturated and causes a discomfort, granular feeling to a wearer due to the excessive amount thereof.

The water-soluble substance 45 only needs to be soluble in urine and has no other limitations in particular. Preferably, however, the water-soluble substance 45 is relatively lower than the temperature changing substance 40 in rate of solution in urine by contact with the urine, so that urine can be retained in the upper layer of the layer 46 containing the water-soluble substance 45 on first urination to thereby facilitate dissolution of the temperature changing substance 40 in a sufficiently effective manner.

The water-soluble substance 45 may be water soluble resin, sugar alcohol, or starch, for example. Specifically, preferred water soluble resins include: polyvinyl alcohol, polyvinyl alcohol containing a polyoxyalkylene group, polyvinyl pyrrolidone, polyalkylene oxide, starch-based resin, carboxymethyl cellulose, methyl cellulose, polyethylene oxide, polysaccharide, hydroxyethyl cellulose, alginate soda, polyacrylic soda, polyacrylic ester, polyacrylamide, polyacrylic acid, vinyl ether polymer, cellulose derivative, ethyl cellulose, hydroxyethyl cellulose, hydroxypropyl cellulose, hydroxypropyl methylcellulose, hydroxypropyl ethylcellulose, ethyl hydroxyethyl cellulose, alginate sodium, dextrin, polyvinyl ether resin, isobutylene, maleic anhydride copolymer, and the like. Preferred sugar alcohols include: xylitol, erythritol, sorbitol, maltitol, isomalt, mannitol, glycerin, lactitol, and the like. Preferred starches include: potato starch, wheat starch, maize starch, rice starch, sweet potato starch, tapioca starch, and the like.

The water-soluble substance 45 is provided in the form of a sheet-like shaped body mainly made of the water-soluble substance 45 (refer to FIG. 15) or in the form of a sheet-like shaped matter supporting the water-soluble substance 45. That is, the water-soluble substance 45 may be solved and formed into a flexible sheet-like matter or may be supported by a sheet of nonwoven fabric, paper, or the like. In particular, if the water-soluble substance 45 may be supported on a base material made of a sheet of nonwoven fabric, paper, or the like, by fixing the powder water-soluble substance 45 to the sheet material; impregnating the sheet material with a water solution of the water-soluble substance 45 or applying the solution to the sheet material, and then drying the sheet material; or applying the fused water-soluble substance 45 to the sheet material.

The layer 46 containing the water-soluble substance 45 is preferably made by fusing the water-soluble substance 45 and forming the same into a flexible sheet-like matter. This provides the layer 46 with a liquid retention property of retaining a liquid until the water-soluble substance 45 is dissolved, and a liquid passage inhibition property specific to a sheet-like shaped body. To verify the liquid passage inhibition property, comparative experiments of air permeability rate were conducted. Normally, comparative experiments of liquid permeability rate should be carried out, but actually not. This is because the experiments with liquid passing would be affected by two factors of liquid retention and liquid passage inhibition. Therefore, this time the experiments of air permeability rate were carried out to make comparisons only in the term of liquid passage inhibition. At the experiments, a Gurley Densometer was used to measure air permeation resistances (Gurley) of test specimens in compliance with JIS P 8117: a sheet-like matter with powdery and particulate sorbitol supported in an air-laid nonwoven fabric layer (350 g/m$^2$ per sheet, 3 mm thick); an oblate layered body formed by overlaying an oblate material (19 g/m$^2$ per sheet, 0.0175 mm thick) mainly made from potato starch on the foregoing sheet-like matter; and crepe paper (20 g/m$^2$ per sheet, 0.1 mm thick, 16-sheet layered). The experiments have revealed that the oblate layered body had several orders of magnitude higher in air permeation resistance than the sheet-like matter and the crepe paper, as shown in Table 1 below. Accordingly, it has been verified that laminating the oblate material improved significantly the sheet-like matter in air permeation resistance and inhibited passage of a liquid. Therefore, if the layer 46 containing the water-soluble substance 45 is formed as a sheet-like shaped body structure of oblate or the like, the water-soluble substance 45 is capable of inhibiting liquid permeation.

TABLE 1

| Type of layer 46 | Crepe paper (second/16 sheets/300 cc) | Sheet-like matter (second/one sheet/300 cc) | "oblate" layered body (second/one sheet/300 cc) |
|---|---|---|---|
| 1 | 4.54 | 0.78 | 19.28 |
| 2 | 5.02 | 0.88 | 24.59 |
| 3 | 4.38 | 0.90 | 21.49 |
| Average | 4.65 | 0.85 | 21.79 |

In addition, a sheet-like matter with the powdery and particulate water-soluble substance 45 supported in at least one layer in the layered sheet of air-laid nonwoven fabric or the like (for example, the sheet-like matter used at the aforementioned air permeation resistance experiments) may be heated, fused, and then cooled and solidified to form a sheet-like shaped body structure, as far as the water-soluble substance 45 can be fused at about 100° C.

However, since the heated and fused substance is prone to spread in a liquid state, the sheet-like shaped body structure may not be formed only by heating the sheet-like matter with the powdery and particulate water-soluble substance 45 supported in the layered sheet. Accordingly, the temperature changing substance in a fused state preferably has a viscosity of 5 to 80 poise (P). With a viscosity of less than 5 P, the temperature changing substance 40 spreads widely when being fused. In contrast, with a viscosity of more than 80 P, the temperature changing substance 40 is low in fluidity when being fused, and remains unmoved even in a fused state. In either case, the sheet-like fused and solidified matter may not be formed in a favorable manner. Since an underpants type disposable diaper generally contains a thermoplastic resin such as polyethylene or polypropylene, the temperature changing substance desirably has a fusing point identical to or less than that of such resins. Out of general thermoplastic resins, polyethylene has a particularly lower fusing point of 100 to 130° C. Accordingly, in this case, the water-soluble substance 45 preferably has a fusing point of 130° C. or less, more preferably 100° C. or less. On the other hand, the water-soluble substance 45 preferably has a fusing point of 70° C. or more so as not to be fused during storage.

For achieving a sufficient liquid retention property, the powdery and particulate water-soluble substance 45 to be fused preferably exists at a rate of about 50 to 300 g/m$^2$ in the layered structure. In addition, the water-soluble substance 45 is preferably contained by 50 wt % or more in the major layers with the water-soluble substance 45.

As foregoing, the layer structure of the water-soluble substance 45 formed by heating and fusing, varies depending on a content of the water-soluble substance 45 in the layers of the layered sheet, a viscosity of the water-soluble substance 45 at the time of heating, and other manufacturing conditions. Therefore, the sheet-like shaped body structure may not be always provided with a liquid passage inhibition property only by heating and fusing, and then cooling and solidifying the substance. Whether the sheet-like shaped body structure has an actually functional liquid passage inhibition property can be determined by the foregoing air permeability rate experiments. In order for the layered sheet having a layer of the water-soluble substance 45 formed by heating and fusing to have the advantage of the present invention (liquid passage inhibition property), the layered sheet needs to possess at least an air permeation resistance of 5 seconds/300 cc or more, preferably an air permeation resistance of 20 seconds/300 cc or more.

Here, if the water-soluble substance 45 capable of being fused at about 100° C. has a property of generating a temperature change by contact with a body fluid to an extent that the change can be perceived by a wearer, the layer 46 containing the water-soluble substance 45 itself changes in temperature by dissolution, thereby achieving a further larger temperature change. In addition, if the sheet-like shaped body structure is formed by fusing and solidifying porous particles with a large surface area, the sheet-like shaped body structure is significantly decreased in surface area and lowered in solution rate. As a result, the layer 46 containing the water-soluble substance 45 can exhibit a liquid passage inhibition property, and even after the sheet-like shaped body is completely dissolved and loses the liquid passage inhibition property, the remaining water-soluble substance 45 is still dissolved slowly. Accordingly, the thermally fused and solidified water-soluble substance 45 (temperature changing substance) exhibits the effect of generating a temperature change for a long time, and the thermally non-fused temperature changing substance 40 remains to be in a particle state and produce the effect of temperature change quickly. Therefore, it is possible to provide a disposable diaper with both fast-acting and slow-acting effects of temperature change.

Such a water-soluble substance with properties of being fusible at about 100° C. and generating a temperature change by contact with a body fluid, may be sorbitol or xylitol, for example. These substances have generally fusing points of about 95 to 110° C. (varying slightly depending on degree of purity).

Further, the separate temperature changing member 47 may not have in advance the particular layer 46 containing the water-soluble substance 45 as the lower layer, as far as the separate temperature changing member 47 has the layer 44 containing the temperature changing substance 40. This is because the layer 46 containing the water-soluble substance in the sheet-like shaped body structure can be generated by heating the separate temperature changing member 47 from the lower layer side to fuse only the lower layer side of the temperature changing substance 40. In such a structure, the fused temperature changing substance 40 is attached or welded to the thermally non-fused particulate temperature changing substance, and then the fused temperature changing substance 40 is solidified. Accordingly, it is possible to fix the thermally fused temperature changing substance and the thermally non-fused temperature changing substance so as not to move in the sheet or slip out from the sheet, whereby the sheet-like material with the separate temperature changing member containing a large quantity of particles can also be easily processed in the diaper manufacturing line.

If the layer 46 containing the water-soluble substance 45 uses an oblate material formed body made of potato starch or the like, when a basis weight of the formed body is too high, the lower layer sheet materials (the absorbent body covering sheet 58 and the like) may become clogged, which may cause problems that moisture absorption of the absorbent body 56 is inhibited or urine spreads out of the absorbent body 56 on second and later urination. Therefore, it is recognized from the results of experiments described below that an optimum basis weight of the oblate material is 24 g/m$^2$ or less, preferably ranges from 15 to 24 g/m$^2$. The experiments were conducted as described below. Firstly, a test specimen of disposable diaper was prepared by disposing an oblate material mainly made of potato starch (19 g/m$^2$ per sheet, 0.0175 mm thick) as the layer 46 containing the water-soluble substance 45 on the upper layer of the absorbent body 56 (pulp of 214 g/m$^2$ and polymer of 214 g/m$^2$) covered with the absorbent body covering sheet 58, and then disposing the face sheet 30 made from polypropylene spun-bonded nonwoven fabric (18 g/m$^2$, with durability and hydrophilic property) on the layer 46. Then, an injection pipe with a 200-g weight was set up on the center of the oblate material, an artificial urine of 75 cc was put into the injection pipe, and a period of time was measured until the artificial urine ran out of the injection pipe. The injection pipe is made from acrylic resin, includes a square-shaped base part of 10 cm on each side and a cylindrical injection part with an inner diameter of 25 mm on the base part, and weighs 100 g (that is, the total weight of the pipe is 300 g including the weight). Time measurement was carried out for each of three successive injections at five-minute intervals. The experiments have revealed that, at the first injection, the case with the oblate material had a longer liquid permeation time and thus was more effective in retaining urine in the sheet, as compared with the case with no oblate material as shown in Table 2. The experiments have also revealed that, at the second and later injections, the specimen with the oblate material and the specimen with no oblate material were comparable in liquid permeation time. Accordingly, it has been proven that the layer 46 containing the water soluble substance 45 with a basis weight of about 19 g/m$^2$ would exhibit a necessary and sufficient liquid retention property.

TABLE 2

| No. of injection | Period of time with no oblate material (s) | Period of time with oblate material (s) |
|---|---|---|
| 1st | 22.41 | 44.56 |
| 2nd | 48.40 | 46.53 |
| 3rd | 61.72 | 63.27 |

Meanwhile, if the layer 44 containing the temperature changing substance 40 as the upper layer is formed by a material with a liquid retention property (a sheet-like matter with the temperature changing substance 40 supported in an absorptive base material, for example), the layer 46 containing the water-soluble substance 45 is preferably increased in basis weight so that the layer 44 containing the temperature changing substance 40 can exhibit sufficiently a liquid retention property.

Instead of providing the separate temperature changing member 47 with regard to temperature change, the absorbent article may be configured in such a manner as shown in FIG. 16 that: the absorbent body 56 has a multi-layer structure with three or more layers, a three-layer structure in the illustrated example; a layer of the absorbent body on the face sheet 30 side, that is, an upper layer absorbent body 56A contains the temperature changing substance 40; a layer under the upper layer of the absorbent body, that is, an intermediate absorbent body 56B contains the water-soluble substance 45; and a lower layer absorbent body 56C is layered under the intermediate absorbent body 56B.

In this case, the absorbent body 56 may be structured by forming the intermediate absorbent body 56B as a shaped body mainly made from the water-soluble substance 45 or as a liquid pervious sheet-like matter with the water-soluble substance 45 supported, and laminating in order three (or more) absorbent body layers including the intermediate absorbent body 56B. Alternatively, the absorbent body 56 may be structured by forming the intermediate absorbent body 56B as a layer containing the particulate water-soluble substance 45 or as a layer made from the particulate water-soluble substance 45 (in this case, the intermediate absorbent body 56B constitutes a simple "intermediate layer" in the strict sense, not an "intermediate absorbent body" but is still called "intermediate absorbent body" for sake of convenience); laminating the intermediate absorbent body 56B and at least the upper and lower layers and then heating the lamination to thereby fuse the water-soluble substance 45; and solidifying the laminate, so as to provide the intermediate absorbent body 56B with the same structure as the sheet-like shaped body. In the latter case, the intermediate absorbent body 56B may be formed by laminating the lower layer absorbent body 56C and sprinkling or projecting the particulate water-soluble substance 45 to the lower layer absorbent body 56C, or the intermediate absorbent body 56B may be formed by laminating an absorbent body containing the particulate water-soluble substance 45 onto the lower layer absorbent body 56C. The temperature changing substance 40 may be contained in advance in the upper layer absorbent body. Alternatively, if a fusing point of the temperature changing substance 40 is the same as or close to that of the water-soluble substance 45, the particulate temperature changing substance 40 may be sprinkled or projected to the upper surface of the upper layer absorbent body 56A after heating so as to avoid the temperature changing substance 40 from being fused. As a matter of course, in the case where the upper layer absorbent body 56A contains the particulate temperature changing substance 40 and the intermediate absorbent body 56B contains the particulate water-soluble substance 45, the absorbent body may be heated from the lower side to thereby form most of the water-soluble substance 45 into a fused and solidified layer and maintain most of the temperature changing substance 40 in particle form.

<Embodiment in Relation to Welding of the Temperature Changing Substance>

As shown in FIGS. 17 to 20, the disposable diaper may be configured in such a manner that: the temperature changing substance is welded in a width-direction central area of the absorbent body 56, at least at a part ranging from the crotch portion to the ventral side portion; and no temperature changing substance is welded in a periphery of a welded section 48 of the temperature changing substance in the absorbent body 56. In a welded state, the temperature changing substance does not move but function reliably in a predetermined region (the crotch portion in this case). In addition, the temperature changing substance is higher in firmness (stiffness) at the welded section than the non-welded section. Therefore, the diaper is less prone to be deformed by wrinkles, bending, or the like at the temperature changing substance welded section that holds reliably the temperature changing substance, and thus can be favorably fit to the body of a wearer at the part ranging from the crotch portion to the ventral side portion.

Stiffness here refers to a bending stiffness (degree of stiffness) and is measured by a method described below in compliance with JIS K 7171 (plastic-bending stiffness test method). Here, a bending stiffness of the inner body 20 is measured in the front-back direction of the diaper using a Tensilon tester (indenter foot's curvature radius R1=5.0±0.1 mm, and a support plate leading end's curvature radius R2=5.0±0.2 mm). A test specimen is prepared by removing resilient and elastic members from the inner body 20 which may exert an influence on measurement results, and then cutting off a square 80 mm long by 50 mm wide from the inner body 200 with respect to the diaper. In the unit of a bending stiffness, 50 mm denotes a length of a shorter side of the specimen and also a width of the specimen deflected by the tester indenter. A pair of support plates has individual leading ends arc-shaped in cross section. The leading ends are in parallel to each other, are aligned in height, and have a clearance of 50 mm therebetween (upper ends). The specimen is placed across the support plates in such a manner that the longer side thereof is orthogonal to the plates. The indenter is arranged such that a foot thereof slightly contacts the specimen. Then, the indenter is descended to obtain a load-deflection curve of the specimen under the conditions: a load cell of 5 kg (range 196 cN) and a speed of 30 mm/min. A maximum value of obtained bending stress is set as a bending stiffness value (cN/50 mm). If a size of a portion to be measured is smaller than the foregoing sampling dimensions, a smaller-scale specimen is used and measured values are converted by proportional calculation on the basis of a dimensional ratio.

The absorbent body 56 has preferably a stiffness of 15 to 50 cN/50 mm, in particular 20 to 35 cN/50 mm at the temperature changing substance welded section 48, and has preferably a stiffness of 5 to 35 cN/50 mm, in particular 10 to 25 cN/50 mm at the temperature changing substance non-welded section in the periphery of the welded section. In general, a difference in stiffness between the welded section 48 and the peripheral section is about 10 to 25 cN/50 mm.

If the absorbent body 56 covers at least a range of 0.15 to 0.80L (L denotes a product length) from the waist side end edge of the ventral side portion to the crotch portion, the temperature changing substance welded section 48 preferably covers at least a range 40Y of 0.25 to 0.45L from the waist side end edge of the ventral side portion to the crotch portion. With such a size, the temperature changing substance welded section 48 can be situated in a position suitable for male and female urination points. That is, on urination, the urine can contact reliably the temperature changing substance welded section 48.

In addition, the temperature changing substance welded section 48 is preferably shaped so as to extend along the groin portion, have a larger width than that of the groin portion, and become further wider with increasing proximity to the waist side. In FIG. 20, reference numeral 49 denotes a wider portion. By shaping the temperature changing substance welded section 48 in such a manner, the diaper can be less prone to be wrinkled longitudinally at the crotch portion and along the groin portion, thereby achieving an enhanced fit in an area ranging from the crotch portion to the ventral side portion. Although the part at the back of the wider portion 49 has a constant width in the illustrated embodiment, the part may also be shaped in a curve along the legs.

If a narrower portion 56N is provided along the legs to the crotch portion of the absorbent body 56, the narrower portion 56N is preferably configured in such a manner that: the narrower portion 56N has a front-back direction length of 0.2 to 0.3Y (Y denotes a front-back direction length of the absorbent body 56); a narrowest part of the narrower portion 56N has a width of 0.6 to 0.75X (X denotes an entire width of the absorbent body 56 and is identical to W2 described above); the waist side end edge of the temperature changing substance welded section 48 in the ventral side portion has a width 40W of 0.4 to 0.7X; the crotch side end of the wider portion 49 in the temperature changing substance welded section 48 is located at the position of the narrowest part of the narrower portion 56N or located nearer the ventral side than the narrowest part; the rear end of the temperature changing substance welded section 48 is located at the position of the rear end of the narrower portion 56N or located nearer the back side than the same; and the rear end of the narrower portion 56N has a width 40X that is 0.7 time or less the width 40W of the waist side end edge of the temperature changing substance welded section 48 and is 0.5X or less. Particularly in the case of an underpants type disposable diaper such as in this embodiment, the waist side end edge of the temperature changing substance welded section 48 is preferably positioned nearer the waist side than the lower end of the side seal section in the ventral side portion.

If the size of the absorbent body 56 falls within the foregoing ranges, the absorbent body 56 can be easily fit around the legs. In addition, the width 40W of the waist side end edge of the welded section 48 in the ventral side portion falls within the foregoing range and the crotch side end of the wider portion 49 in the temperature changing substance welded section 48 is positioned in the foregoing range in the front-back direction, it is possible to prevent effectively that the diaper is wrinkled along the groin portion due to a wearer's walking. In addition, if the rear end of the temperature changing substance welded section 48 falls within the foregoing range in the front-back direction, there is no need to dispose an unnecessary temperature changing substance at the gluteal portion that is less sensitive to temperature changes. Further, if the width 40X of the rear end of the temperature changing substance welded section 48 falls within the foregoing range, the diaper is preferably less prone to be wrinkled longitudinally at the crotch portion.

The absorbent body 56 with the temperature changing substance welded can be manufactured by placing the temperature changing substance in an arbitrary form such as particulate form (including powdery form) or fibrous form on the upper surface of the absorbent body 56 at a predetermined site or entering the same into the absorbent body 56 at a predetermined site, heating the temperature changing substance together with the absorbent body 56, fusing only the temperature changing substance and attaching the same to the fibers of the absorbent body 56, and then cooling and solidifying the temperature changing substance.

In this embodiment, preferably, within the absorbent body covering sheet 58 of the absorbent structure 50, the temperature changing substance is disposed on the face side layer of the absorbent body 56 containing the high absorbent polymer at least in the face side layer, and the temperature changing substance is welded to the upper surface or the face side layer of the absorbent body. In such a configuration, urine having passed through the face sheet 30 and reached the upper surface of the absorbent body 56, is cooled or heated by the temperature changing substance, and then absorbed by the high absorbent polymer contained in the face side layer. Accordingly, the temperature of the face side layer of the absorbent body 56 containing the high absorbent polymer can be effectively transferred to the surface of the article to allow a wearer to perceive the temperature change.

Such an embodiment in which the particulate temperature changing substance is provided to (placed on or entered into) the upper surface or the face side layer of the absorbent body 56, can be produced, for example, by forming the absorbent body 56 containing the high-absorbent polymer particles in the virtually entire thickness direction, and sprinkling or projecting the particulate temperature changing substance onto the upper surface of the absorbent body 56 at a predetermined site. In particular, by projecting the particulate temperature changing substance, part of the temperature changing substance enters the absorbent body 56. Therefore, the absorbent body 56 has a mixture of the temperature changing substance and the high absorbent polymer within the face side layer, and has a layer containing virtually only the temperature changing substance on the face side layer. In such a formation, part of the temperature changing substance is preferably welded to the absorbent body in a mixed state to thereby prevent the welded section 48 from being too hard. Alternatively, in order for a wearer to sense a temperature change immediately after urination in a clearer manner, the temperature changing substance may be sprinkled such that the foregoing mixed layer is not formed but almost all the temperature changing substance 40 is disposed on the upper side of the absorbent body 56.

Out of the high-absorbent polymer particles generally contained in the absorbent body 56, this embodiment uses the particles resided in the face side layer to absorb and retain temperature-changed urine. Therefore, in this embodiment, when the density of the high absorbent polymer is higher on the face side than the back side, the absorbent body 56 preferably can retain more cooled or heated urine in the face side and generate a larger temperature change on the surface of the article. More preferably, when the absorbent body 56 is formed with a density gradient such that the high absorbent polymer becomes gradually higher in density with increasing proximity to the face side of the absorbent body 56 or the high absorbent polymer becomes higher in density in a step-by-step manner with increasing proximity to the face side of the absorbent body 56, the absorbent body 56 is significantly effective in achieving a temperature change on the surface of the article. Such a density gradient can be formed by a high absorbent polymer having a particle size distribution with a high content of large-sized particles that are less prone to enter the absorbent body 56.

As shown in FIG. 21, the absorbent body 56 may be configured in such a manner that: a two-layer structure is formed so as to have the upper layer 56A provided in the central portion in the width-direction of the absorbent body 56 at least at a part ranging from the crotch portion to the ventral side portion, and the lower layer 56B in contact with the backside of the upper layer 56A; and the temperature changing substance is welded to the entire upper layer 56A (entirely in a direction orthogonal to the thickness direction) to thereby form the temperature changing substance welded section 48 only by the upper layer 56A. Such a structure can be produced in such a manner that the upper layer 56A is formed by accumulating short fibers of pulp or the like mixed with the temperature changing substance, or a sheet containing the temperature changing substance is cut or folded into a predetermined shape, and only the upper layer 56A is heated and cooled or the upper layer 56A and the lower layer 56B are integrally heated and cooled.

There is no particular limitation on a heating means used in the foregoing production method, and FIGS. 22 to 25 show examples of such heating means. Each of the heating means in FIGS. 22 and 23 uses an air-through dryer for generating a heating effect by passage of high-temperature air. In the case of using the means in FIG. 22, while the absorbent body 56 with the temperature changing substance at a predetermined portion is moved on a belt conveyor 301, the absorbent body 56 is heated by hot wind 302 passing in a direction orthogonal to a transfer plane and then is cooled by wind 303 also passing in the direction orthogonal to the transfer plane. In the case of using the means in FIGS. 23 (*a*) and 23 (*b*), while the absorbent body 56 with the temperature changing substance at a predetermined portion, which is wound around a suction roll 311 installed in a heating chamber 310 to which high-temperature air is supplied, is conveyed, the absorbent body 56 is heated by hot wind 312 passing from outside to inside the suction roll 311, and then the absorbent body 56 is transferred and cooled in a state of being wound around a cooling roll 313 installed outside the heating chamber 310.

In addition, in the case of using the heating means in FIG. 24, while the absorbent body 56 with the temperature changing substance at a predetermined portion is wound around a heating roll 320 and conveyed, heat from the heating roll 320 is transferred to the temperature changing substance of the absorbent body 56 by contact with the absorbent body 56 to thereby allow the absorbent body 56 to be heated from one side.

Further, in the case of using the heating means in FIG. 25, the absorbent body 56 with the temperature changing substance at a predetermined portion is passed between a pair of rolls 330 and 331, or 340 and 341 at least one of which is a heating roll, thereby to transfer heat from the heating rolls to the temperature changing substance by contact with the absorbent body 56 and heat the absorbent body 56. In this case, the absorbent body 56 may be formed so as not to have a convex-concave surface using the smooth rolls 330 and 331 with a flat and smooth surface as shown in FIG. 25 (*a*), or the absorbent body 56 may be formed so as to have a convex-concave surface on one side using the emboss roll 340 with a predetermined convex-concave pattern, for one of the rolls, as shown in FIG. 25 (*b*). Particularly in the latter case, the absorbent body 56 may be preferably configured by forming the temperature changing substance welded section 48 in a convex pattern of the emboss roll 340, and then heating only the section 48. In this configuration, since the welded section

48 is formed only in a region corresponding to the convex pattern of the emboss roll 340, the temperature changing substance may be disposed in a wider area than the convex pattern of the emboss roll 340. As stated above, this approach of heating partially the absorbent body 56 eliminates the need to dispose the temperature changing substance only in a predetermined region of the absorbent body 56. For example, the welded section 48 can be formed by disposing the temperature changing substance on the entire absorbent body and heating the absorbent body only in a predetermined region.

The temperature changing substance can be heated and fused not only at the time of production of the absorbent body 56 but also at any stage of subsequent processes in the manufacture of the diaper. For example, the temperature changing substance may be heated and fused in the inner body or the completed diaper, upon completion of assembling of the inner body 200 (before assembling of the diaper product) or upon completion of assembling of the diaper product. In this case, heating may be conducted by using the foregoing means shown in FIGS. 22 to 25, for example.

The temperature changing substance is supposed to be welded by heating, and therefore is preferably lower in fusing point than other members heated together with the temperature changing substance. Since an underpants type disposable diaper generally contains a thermoplastic resin such as polyethylene or polypropylene, the temperature changing substance desirably has a fusing point identical to or less than that of such resins. Out of general thermoplastic resins, polyethylene has a particularly lower fusing point of 100 to 130° C. Accordingly, in this case, the temperature changing substance preferably has a fusing point of 130° C. or less, more preferably 100° C. or less. On the other hand, the temperature changing substance preferably has a fusing point of 70° C. or more so as not to be fused during storage of the product. Such a temperature changing substance may be sorbitol or xylitol, for example, generally with a fusing point of about 95 to 110° C. (varying slightly depending on degree of purity).

In addition, if the temperature changing substance is low in viscosity at the time of fusion, the temperature changing substance is less prone to penetrate between the fibers of the absorbent body 56 and therefore is decreased in adhesion to the absorbent body 56. From this viewpoint, the temperature changing substance preferably has a viscosity of 5 to 80 poise at a fusing temperature (for example, 70 to 130° C.).

Having been welded into liquid form and solidified, the temperature changing substance welded to the absorbent body 56 is decreased in surface area. Accordingly, the temperature changing substance is decreased in area of contact with urine, which controls a rate of temperature change and improves durability of a temperature-changed state. However, if a rate of temperature change is slowed uniformly, a wearer may not perceive a temperature change easily. Therefore, in a preferred embodiment, a particulate matter with a low bulk density is used as a temperature changing substance, and part of the substance is fused to form a solid matter with a high bulk density, and the remaining non-fused object remains as a particulate matter with a low bulk density. The particulate temperature changing substance with a lower bulk density tends to be larger in surface area and higher in efficiency of contact with urine than that with a higher bulk density, if those substances are at the same level in particle size, and therefore produces a higher rate of temperature change. In particular, this tendency is prominent if the temperature changing substance is dissolved in urine to generate a temperature change. Accordingly, as described above, if only part of the temperature changing substance is fused, the temperature changing substance kept in particulate form exhibits the effect of a temperature change quickly, and the fused and solidified temperature changing substance generates the effect of a temperature change at a lower rate. This achieves both fast-acting and slow-acting temperature changes.

The particulate temperature changing substance with a low bulk density is preferably porous particles such as granules, particles with a large number of surface asperities, and particles with fine pores on surface or inside. A bulk density of the particles may be decided as appropriate, but is preferably 50% or less of a real density of the same (having a gap (space) of 50% or more of an apparent volume of the same). For example, sorbitol has a real density of 1.50 g/cm$^3$, and therefore a preferred bulk density of the same is 0.75 g/cm$^3$ or less, more preferably 0.50 to 0.70 g/cm$^3$, in particular preferably 0.55 to 0.65 g/cm$^3$. In addition, particles with a large size are low in apparent bulk density and are not large in surface area. Accordingly, the particulate temperature changing substance preferably has an average particle size of 200 to 600 μm (JIS K 1474-2007, median diameter).

Meanwhile, if the absorbent body 56 has a two-layer structure in which the upper layer 56A has the temperature changing substance welded section 48, the upper layer 56A preferably contains the high absorbent polymer and is higher in fiber density than the lower layer 56B. If there is a difference in fiber density between the two layers, the fiber density of the upper layer 56A is preferably in particular 4.5 times or more that of the lower layer 56B. Specifically, the fiber density of the upper layer 56A is 2.25 to 6.75 g/m$^3$, and the fiber density of the lower layer 56B is about 0.5 to 1.5 g/m$^3$. FIG. 26 shows results of experiments of liquid retention property with varied fiber density ratios. At the experiments, a lower layer was prepared from an air-through nonwoven fabric with a density of 1.0 g/m$^3$ (dimensions of 10×15 cm and a basis weight of 25 g/m$^2$), and upper layers were prepared from layers made of only pulps with various densities (dimensions of 10×15 cm, a basis weight of 200 g/m$^2$). Each of the upper layers was weighed in advance. Then, the upper layer was overlaid on the lower layer in a horizontal plane, and water of 10 ml in a beaker was poured from a 2-cm height onto the upper layer in 10 seconds. After a lapse of five minutes since the pouring, the water-absorbing upper layer was weighed. The pre-absorption weight was subtracted from the post-absorption weight to determine an amount of water absorption, and then the amount of water absorption was divided by an amount of injected water to determine a liquid retention ratio of the upper layer. From the results, it has been understood that: with a small difference in fiber density, the liquid retention ratio of the upper layer was about 40%; when the fiber density of the upper layer reached about 4.0 times the fiber density of the lower layer, the liquid retention ratio of the upper layer started to rise highly; and when the fiber density of the upper layer was 4.5 times or more of the fiber density of the lower layer, the liquid retention ratio of the upper layer exceeded 50% despite location on the upper side, thereby allowing urine absorbed in the upper layer to be less prone to move to the lower layer.

With such a configuration, most of urine from first urination can be retained in the upper layer 56A until the high absorbent polymer starts to exert absorption capability and take up urine in the upper layer 56A. As a result, the urine in the upper layer 56A is kept in contact with the temperature changing substance until being absorbed by the high absorbent polymer, and is less prone to move to the lower layer 56B, thereby generating a larger temperature change. In addition, since the urine with a sufficient temperature change is absorbed and retained by the high absorbent polymer in the upper layer 56A, it is possible to transfer the temperature change effectively to a wearer and reduce back-flow of the urine to the skin of the wearer. In addition, the upper layer 56A has preferably an initial absorption capacity at least to an extent that an amount of urine for one urination can be all retained. Accordingly, all urine on first urination with a temperature change can be retained in the upper layer 56A, without moving to the lower layer 56B to waste the temperature change. For setting the initial absorption capacity for one urination, if the upper layer 56A is based on pulp material, it is appropriate that the upper layer 56A has a pulp content of 5 to 10 g, and has weight proportions of fibers, high absorbent polymer, and temperature changing substance of about 15 to 30%, about 5 to 40%, and about 30 to 80%, respectively. The upper layer 56A preferably has basis weights of fibers, high absorbent polymer, and temperature changing substance of 150 to 300 g/m$^2$, 50 to 400 g/m$^2$, and 300 to 800 g/m$^2$, respectively.

Toilet training diapers are not necessarily required to have an absorption capacity in excess of the foregoing level because the diapers are replaced if a wearer can perceive his/her urination and inform that to his/her parent on first urination. However, if the wearer cannot perceive his/her own urination or cannot inform that to his/her parent, or if diapers are not replaced immediately, the diapers need to absorb urine on second and later urinations. Even in such a case, this embodiment allows the lower 56B to absorb urine, in place of the upper layer 56A having been saturated with the urine on first urination.

The initial absorption capacity here refers to an amount of water (or a body fluid such as urine or the like) that can be temporarily absorbed and retained until an absorptive material such as a fiber aggregate or high absorbent polymer (SAP) starts to exert a full absorption capability. The high-absorbent polymer particles and the water soluble temperature changing substance have each an initial absorption capacity of 1 cc per 1 g. Meanwhile, since cellulose-based fiber such as pulp and olefin-based synthetic fiber hardly change in absorption capacity even after long-time absorption, the initial absorption capacity of such a fiber material can be determined by setting a water retaining capacity per 1 g as an initial absorption capacity per 1 g, and adding up the initial absorption capacity in accordance with the amount of the fiber material. In the present invention, the upper layer 56A in the absorbent body 56 preferably has an initial absorption capacity of 70 cc or more, more preferably 100 cc or more (not including an absorption capacity of the absorbent body covering sheet 58).

In addition, in order for the upper layer 56A to retain most of urine on first urination, fibers constituting the upper layer 56A are also preferably higher than fibers constituting the lower layer 56B in a degree of hydrophilicity and/or water retention capacity. The fibers constituting the upper layer 56A preferably have a water retention capacity of 8 cc/g or more, in particular preferably 10 cc/g or more. The fibers constituting the lower layer 56B preferably have a water retention capacity of 8 cc/g or less, in particular preferably 5 cc/g or less.

(Method of Measuring the Water Retention Capacity of 1-G Fiber)

1. Put ion-exchange water of 200 cc at 20° C. into a 200-cc beaker.
2. Put a fiber aggregate of 1 g into the beaker, and stir the water with a glass rod for 30 seconds.
3. Set a Buchner funnel with an inner diameter of 62 mm on a support base, and pour the specimen with the water from the beaker into the funnel in 10 seconds for natural filtration.
4. Place a cylindrical weight with a bottom of 60 mm in diameter and a weight of 1,450 g on the specimen, and leave the specimen as it is for one minute. (A load per 10-cm square is 5 kg).
5. Weigh the fiber, and determine the water retention capacity of the fiber (1 g=1 cc) from a difference in weight between before and after water retention. Convert the water retention capacity into a value per 1-g fiber. The resultant value is set as the water retention capacity per 1-g fiber.

If the specimen is a sheet-like matter of nonwoven fabric or the like, the sheet of 1 g is cut to a piece 20 mm long, 2 mm wide, and 2 mm thick, or a smaller size.

<Embodiment in Relation to a Heat-Insulating Layer>

As shown in FIGS. 27 to 29, there is another embodiment in which a heat-insulating layer 57 is interposed between the absorbent body 56 and the liquid impervious sheet 11 (equivalent to the backside sheet). The heat-insulating layer 57 basically may have the same structure as that of the absorbent structure 50. In this embodiment, the heat-insulating layer 57 may be identical in configuration to the absorbent structure 50, or may be different from the absorbent structure 50 as necessary in some of materials, some of dimensions, substance contents, physical properties, and the like. The heat-insulating layer 57 may be configured by various nonwoven fabrics. In particular, fibers constituting the heat-insulating layer 57 are preferably lower in density than fibers constituting the absorbent structure 50.

In a particularly preferred embodiment, the absorbent body 56 and the heat-insulating layer 57 are configured in such a manner that the heat-insulating layer 57 has a fiber density of 0.5 to 1.5 g/m$^3$, the absorbent body 56 has a fiber density of 4.5 times or more the fiber density of the heat-insulating layer 57, in a range of 2.25 to 6.75 g/m$^3$.

FIG. 35 shows measurement results from experiments of liquid retention capacity with varied fiber density ratios. At the experiments, a heat-insulating layer was prepared from an air-through nonwoven fabric with a density of 1.0 g/m$^3$ (dimensions of 10×15 cm and a basis weight of 25 g/m$^2$), and absorbent bodies were prepared from layers made of only pulps with various densities (dimensions 10×15 cm, a basis weight of 200 g/m$^2$). Each of the absorbent bodies was weighed in advance. Then, the absorbent body was overlaid on the heat-insulating layer in a horizontal plane, and water of 10 ml in a beaker was poured from a 2-cm height onto the absorbent body in 10 seconds. After a lapse of five minutes since the pouring, the water-absorbing absorbent body was weighed. The pre-absorption weight was subtracted from the post-absorption weight to determine an amount of water absorption, and then the amount of water absorption was divided by an amount of injected water to determine a liquid retention ratio of the absorbent body. From the results, it has been understood that: with a small difference in fiber density, the liquid retention ratio of the absorbent body was about 40%; when the fiber density of the absorbent body reached about 4.0 times the fiber density of the heat-insulating layer, the liquid retention ratio of the absorbent body started to rise highly; and when the fiber density of the absorbent body was 4.5 times or more the fiber density of the heat-insulating layer, the liquid retention ratio of the absorbent body exceeded 50% despite location on the upper side, thereby allowing urine absorbed in the absorbent body to be less prone to move to the heat-insulating layer.

With such a configuration, most of urine from first urination can be retained in the absorbent body 56 until the high absorbent polymer in the absorbent body 56 starts to exert absorption capability and take up urine. As a result, the urine in the absorbent body 56 is kept in contact with the temperature changing substance 40 until being absorbed by the high absorbent polymer, thereby generating a larger temperature change. In addition, since the urine is less prone to move to the heat-insulating layer 57, the heat-insulating layer 57 can maintain a high heat-insulating property. In addition, since the urine with a sufficient temperature change is absorbed and retained by the high absorbent polymer in the absorbent body 56, it is possible to transfer the temperature change effectively to a wearer and reduce back-flow of the urine to the skin of the wearer. In addition, the absorbent body 56 has preferably an initial absorption capacity at least to an extent that an amount of urine for one urination can be all retained. Accordingly, all urine on first urination with a temperature change can be retained in the absorbent body 56, which makes the heat-insulating layer 57 less prone to be lowered in heat insulating property. In addition, the urine with a temperature change does not move to the heat-insulating layer 57 to waste the temperature change. For setting the initial absorption capacity for one urination, if the absorbent body 56 is based on pulp material, it is appropriate that the absorbent body 56 has a pulp content of 5 to 10 g, and has weight proportions of fibers, high absorbent polymer, and temperature changing substance 40 of about 15 to 30%, about 5 to 40%, and about 30 to 80%, respectively. The absorbent body 56 preferably has basis weights of fibers, high absorbent polymer, and temperature changing substance 40 of 150 to 300 g/m$^2$, 50 to 400 g/m$^2$, and 300 to 800 g/m$^2$, respectively.

Toilet training diapers are not necessarily required to have an absorption capacity in excess of the foregoing level because the diapers are replaced if a wearer can perceive his/her urination and inform that to his/her parent on first urination. However, if the wearer cannot perceive his/her own urination or cannot inform that to his/her parent, or if diapers are not replaced immediately, the diapers need to absorb urine on second and later urinations. Even in such a case, the diaper may be configured such that the heart-insulating layer 57 can absorb urine in place of the saturated absorbent body 56, thereby to make leakage less prone to occur.

The initial absorption capacity is as described above. The absorbent body 56 preferably has an initial absorption capacity of 70 cc or more, more preferably 100 cc or more (not including an absorption capacity of the absorbent body covering sheet 58).

In addition, in order for the absorbent body 56 to retain most of urine on first urination, fibers constituting the absorbent body 56 are also preferably higher than fibers constituting the heat-insulating layer 57 in a degree of hydrophilicity and/or water retention capacity. The fibers constituting the absorbent body 56 preferably have a water retention capacity of 8 cc/g or more, in particular preferably 10 cc/g or more. The fibers constituting the heat-insulating layer 57 preferably have a water retention capacity of 8 cc/g or less, in particular preferably 5 cc/g or less. The method of measuring a water retention capacity per 1-g fiber is as described above.

The heat-insulating layer 57 may be covered together with the absorbent body 56 by the absorbent body covering sheet 58. Preferably, the heat-insulating layer 57 is covered separately from the absorbent body 56, by a heat-insulating layer covering sheet 59 made from a fiber aggregate with a higher fiber density than that of the heat-insulating layer, as shown in the illustrated embodiment. In such a configuration, even if urine having passed through the absorbent body 56 reaches the heat-insulating layer 57, the urine is absorbed and retained in the heat-insulating layer covering sheet 59 and is less prone to be retained in the heat-insulating layer 57, thereby maintaining a heat-insulating property. The heat-insulating layer covering sheet 59 basically may be similar to the absorbent body covering sheet 58. In this case, the heat-insulating layer covering sheet 59 may be configured in absolutely the same manner as the absorbent body covering sheet 58, or may be different from the absorbent body covering sheet 58 as needed in material, dimensions, substance contents, physical properties, and the like.

In addition, the heat-insulating layer 57 is desirably low in liquid retention capacity so as not to attract urine with a temperature change in the absorbent body 56, but may contain the high absorbent polymer, as with the absorbent body 56.

In addition, for a further enhanced heat insulating property, a plurality of heat-insulating layers 57 may be arranged as shown in FIG. 31. If these heat-insulating layers 57 are formed by fiber aggregates, the face-side heat-insulating layer 57 and the backside heat-insulating layer 57 may be formed by aggregates of the same fiber with the same density, or may be formed with a difference in kind or density of fiber, or both. By making the both heat-insulating layers lower at least in fiber density than the absorbent body 56, the heat-insulating layers can produce a further larger heat-insulating effect.

Size and position of the heat-insulating layer 57 can be decided as appropriate from the viewpoint of heat-insulating performance. Desirably, the heat-insulating layer 57 is sized to cover a length of 70% or more of the back surface of the absorbent body 56 both in the front-back direction and width direction (that is, corresponding to the central portion of the absorbent body 56 in the front-back direction and the width direction), and cover an area of 50% or more of the same. The heat-insulating layer 57 may have a larger area than that of the absorbent body 56, and in particular preferably covers the entire backside of the absorbent body 56, thereby resulting in a further larger heat-insulating effect.

The heat-insulating layer 57 exerts a heat-insulating effect if the temperature changing substance 40 is interposed between the face sheet 30 and the heat-insulating layer 57, regardless of a position of substance containment (in the thickness direction and the direction along the face side) and a manner of substance containment. Hereinafter, preferred embodiments will be described in sequence.

FIG. 31 shows a first preferred embodiment which employs the aforementioned structure containing the temperature changing substance shown in FIG. 3. In this case, since the backside of the absorbent body 56 is covered with the heat-insulating layer 57, if the outside air temperature is extremely high (in midsummer or around a heating appliance in wintertime) or extremely low (outdoor in wintertime and the like), the temperature of the urine retained in the absorbent body 56 can be maintained to thereby obtain a desired temperature change. In other respects, this embodiment is identical to the aforementioned structure containing the temperature changing substance shown in FIG. 3.

FIG. 32 shows a second preferred embodiment which employs the aforementioned structure containing the temperature changing substance shown in FIG. 10. The details of this embodiment are as described above.

FIG. 33 shows a third preferred embodiment which employs the structure containing the temperature changing substance shown in FIG. 11. The details of this embodiment are as described above.

The foregoing first to third preferred embodiments each have the aforementioned temperature changing substance 40 and the high absorbent polymer in the absorbent structure 50. Alternatively, as a fourth preferred embodiment different from those embodiments, the structure containing the temperature changing substance shown in FIG. 34 may be employed. The details of this embodiment are as described above.

(Experiments in Relation to a Heat-Insulating Layer)

As test samples, two underpants type disposable diapers with the structure shown in FIG. 27 were prepared. One of the samples (example 1) had the heat-insulating layer 57 formed by a fiber aggregate of opened cellulose acetate tow, with a fiber density of 0.8 g/cm$^3$ and a fineness of 4.4 dtex. The other sample (example 2) had the heat-insulating layer 57 made from a fluff pulp (with no high absorbent polymer) with a fiber density of 3.7 g/cm$^3$. In addition, as a comparative example, a sample identical to the example 1 except for the absence of the heat-insulating layer 57 was prepared. These examples have in common specifications as shown below, except for the kind and the presence or absence of the heat-insulating layer.

(Common Specifications)

Liquid pervious face sheet 30: Air-through nonwoven fabric made from PE/PP composite fibers with a thickness of 2 mm and a basis weight of 25 g/m$^2$ Absorbent body 56: Fluff pulp with a fiber density of 3.7 g/cm$^3$ (containing the dispersed high absorbent polymer)

Size of the absorbent body 56: Covering an area from a position of 205 mm forward to a position of 190 mm backward with respect to the central portion in the front-back direction, and from a position of 70 mm leftward to a position of 70 mm rightward with respect to the central portion in the width-direction. The area is 55,300 mm$^2$, and the thickness is 2 mm.

Absorbent body covering sheet 58: Crepe paper with a thickness of 1 mm and a basis weight of 15 g/m$^2$ Kind of the temperature changing substance 40: Sorbitol ("Sorbit" with heat of solution of −26 cal/g, produced by Towakasei Kogyo Co., Ltd.)

Solubility of the temperature changing substance 40 (in water of 100 ml at 20° C.): 70 g Size of the part having the temperature changing substance 40: Covering a rectangular area from a position of 160 mm forward to a position of 40 mm backward with respect to the central portion in the front-back direction, and from a position of 50 mm leftward to a position of 50 mm rightward with respect to the central portion in the width-direction. The area is 20,000 mm$^2$.

Total amount of change in calorific value possibly caused on the absorbent body by the temperature changing substance 40: 208 cal (in the case with sorbitol of 400 gsm)

Amount of change in calorific value at the part having the temperature changing substance 40 per unit area: 1.04 cal/cm$^2$ (in the case with sorbitol of 400 gsm)

Absorption speed of the high absorbent polymer: 35 seconds

Basis weight of the high absorbent polymer in the absorbent body 56: 150 g/m$^2$ (the polymer is dispersed uniformly in the absorbent body 56 in the thickness direction.)

Size of the part having the high absorbent polymer: The entire absorbent body 56

(Experimental Method and Experimental Results)

Beakers containing hot water at 37° C. were wrapped with each of the samples (the inside of the sample contacted the beaker). The beakers were kept under an atmosphere at a temperature of 20° C. and a humidity of 50% RH, and the temperatures of hot water in the beakers were measured by a thermometer at each predetermined period of time. FIG. 36 shows measurement results. As understood from the graph, the experiments have revealed that the samples of examples 1 and 2 in the present invention were higher in heat-insulating performance and maintained the temperature of the inside of the diaper for a longer period of time, as compared with the comparative example. Consequently, it can be expected that the present invention will bring about the same results in maintaining a temperature change generated by the temperature changing substance.

INDUSTRIAL APPLICABILITY

The present invention is applicable to a wide range of uses such as underpants type absorbent articles, tape type absorbent articles, and pad type absorbent articles.

BRIEF DESCRIPTION OF NUMERALS

Figure 1:
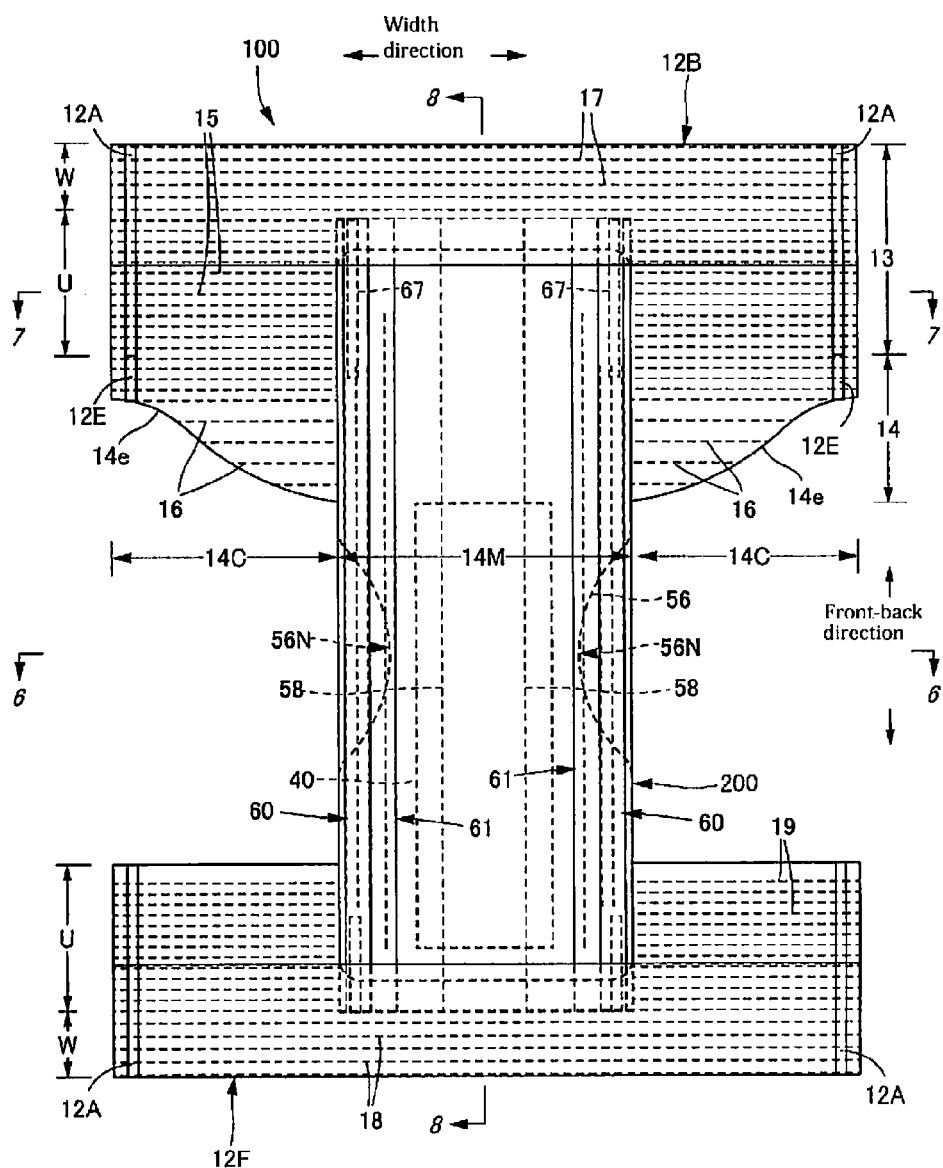
FIG. 1 is a plan view of an inner side of an underpants type disposable diaper in an open state.
Figure 2:
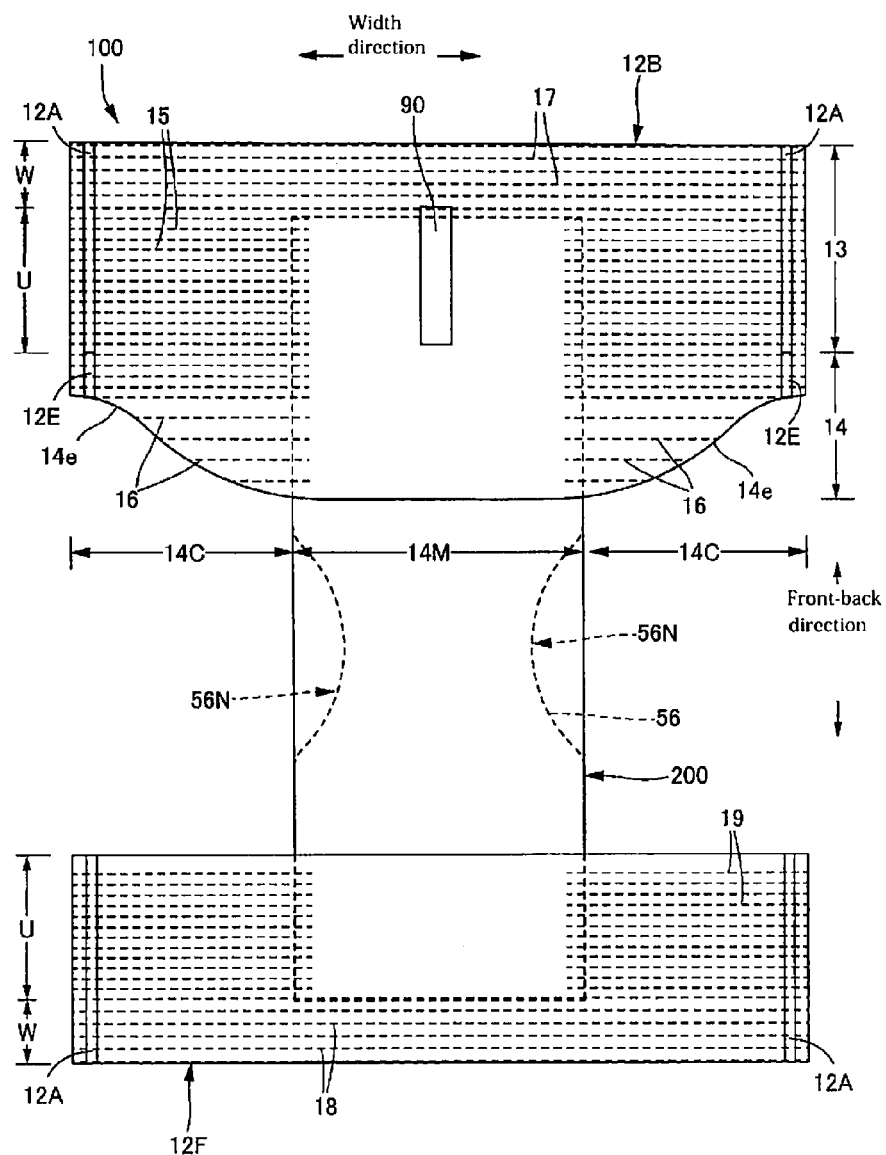
FIG. 2 is a plan view of an outer side of the underpants type disposable diaper in the open state.
Figure 3:
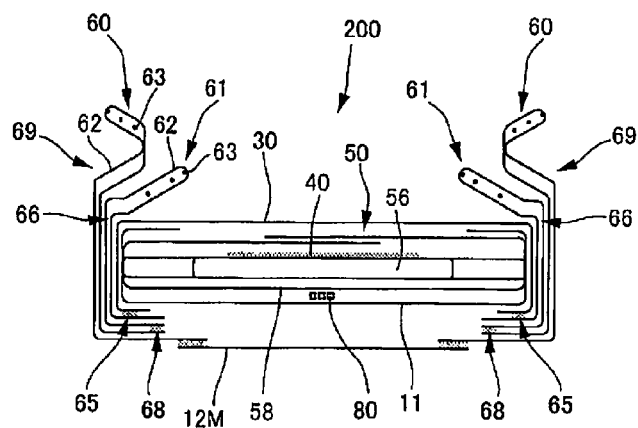
FIG. 3 is a cross-section view of FIG. 1 taken along line 6-6.
Figure 4:
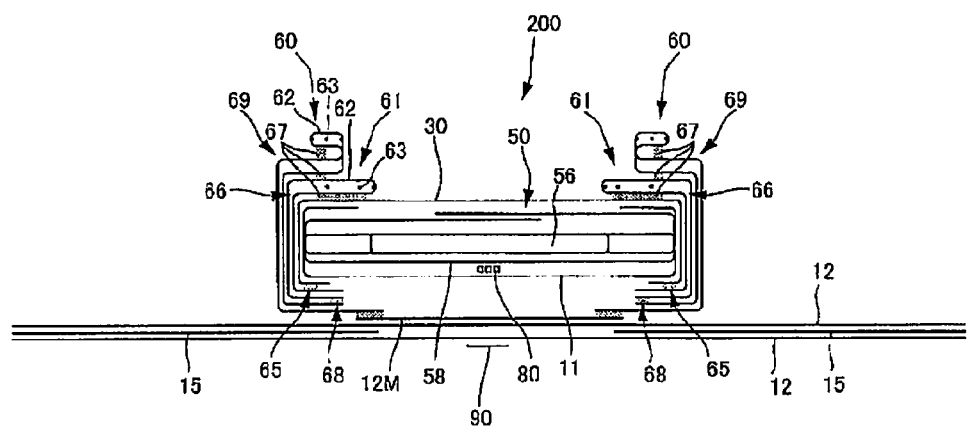
FIG. 4 is a cross-section view of FIG. 1 taken along line 7-7.
Figure 5:
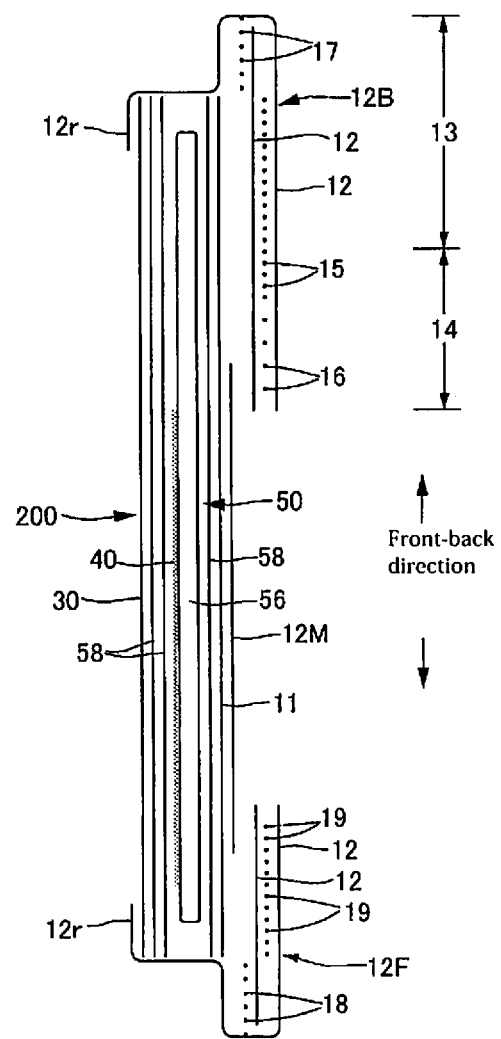
FIG. 5 is a cross-section view of FIG. 1 taken along line 8-8.
Figure 6:
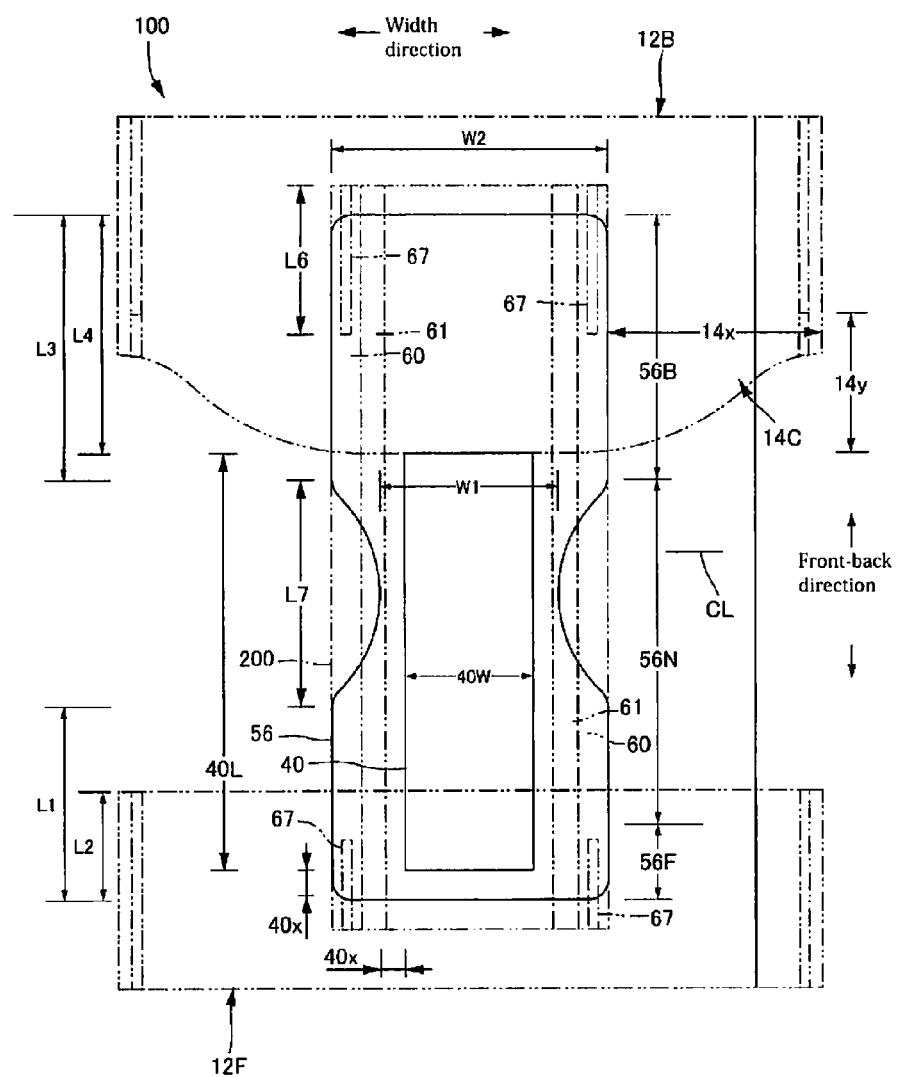
FIG. 6 is a plan view of major components with dimensions of the underpants type disposable diaper in the open state.
Figure 7:
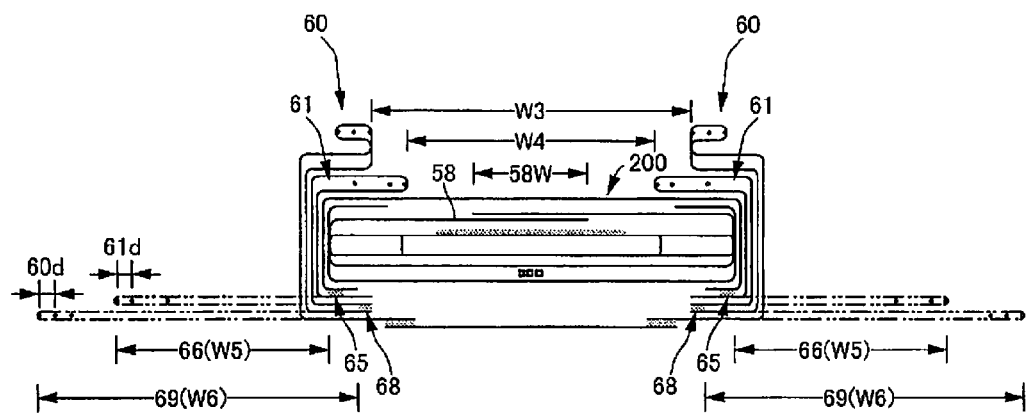
FIG. 7 is a cross-section view of the major components with dimensions of the underpants type disposable diaper.
Figure 8:
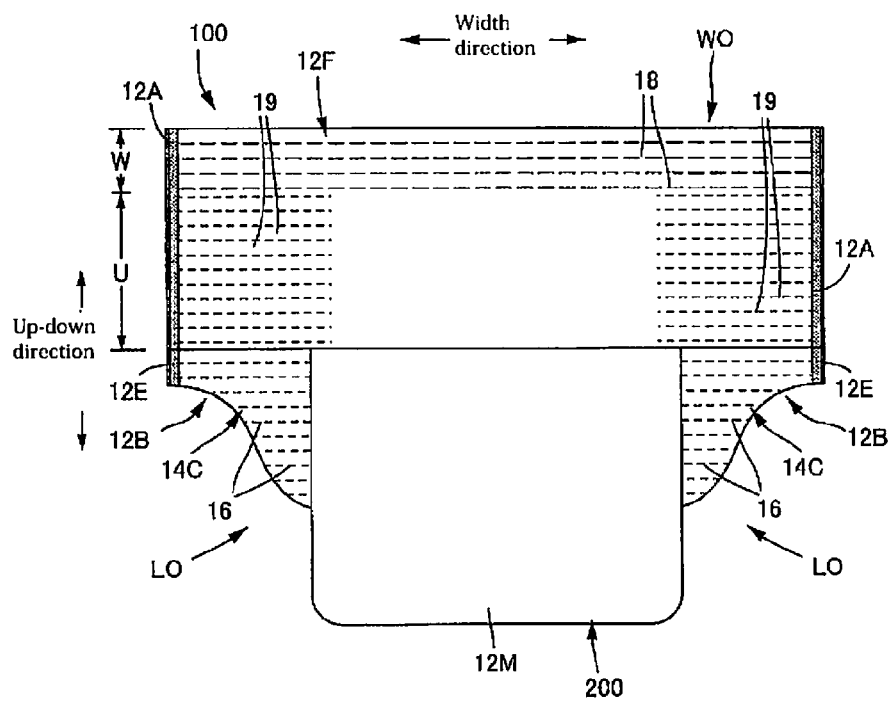
FIG. 8 is a front view of the diaper in a product state.
Figure 9:
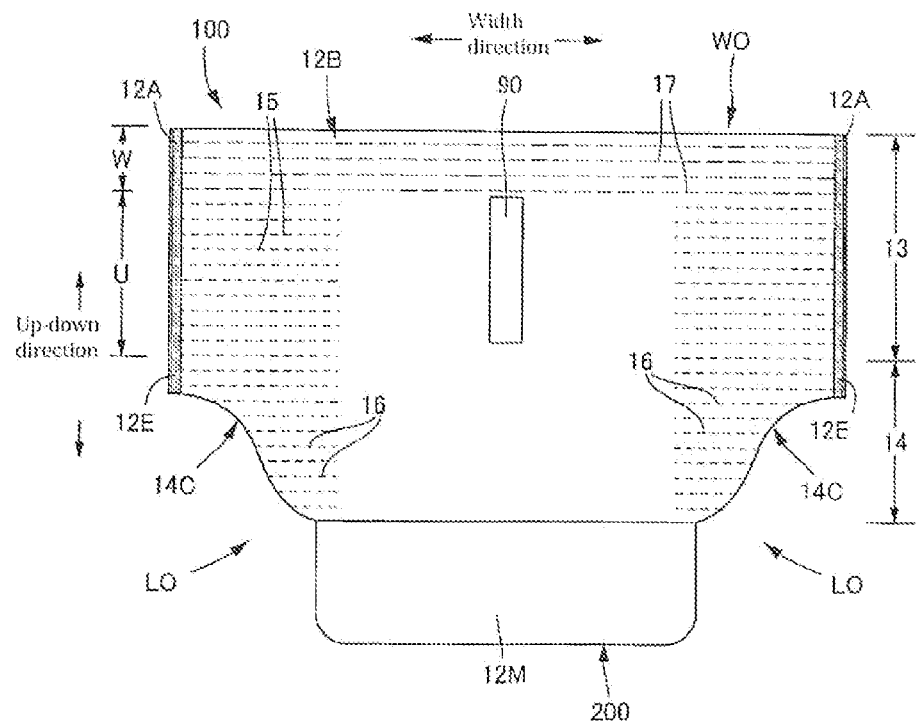
FIG. 9 is a rear view of the diaper in the product state.
Figure 10:
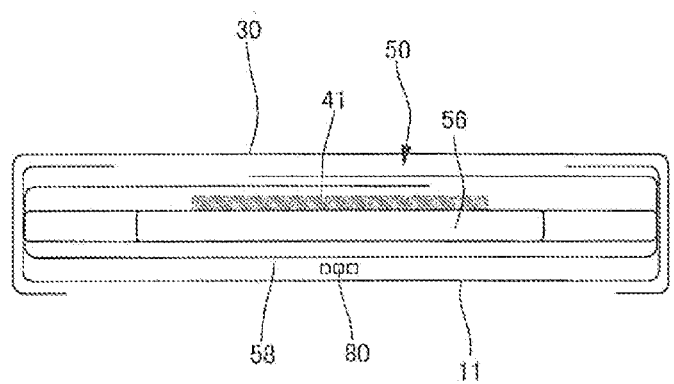
FIG. 10 is a cross-section view of major components of a diaper of another embodiment.
Figure 11:
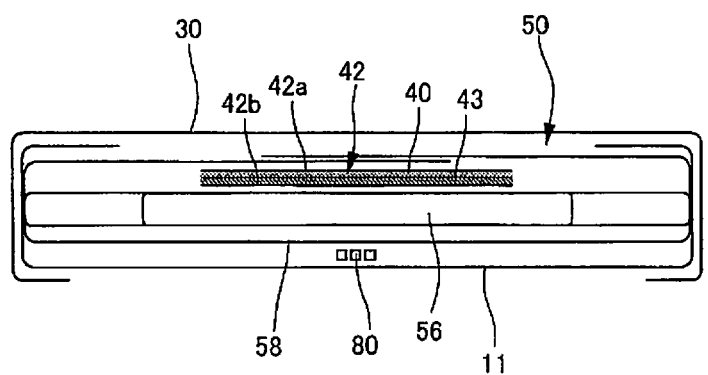
FIG. 11 is a cross-section view of major components of a diaper of still another embodiment.
Figure 12:
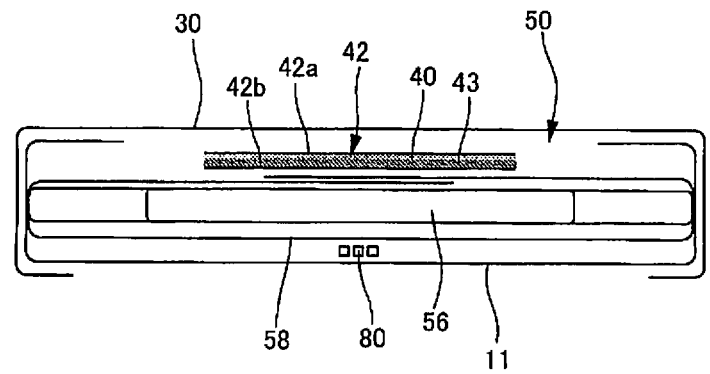
FIG. 12 is a cross-section view of major components of a diaper of still another embodiment.
Figure 13:
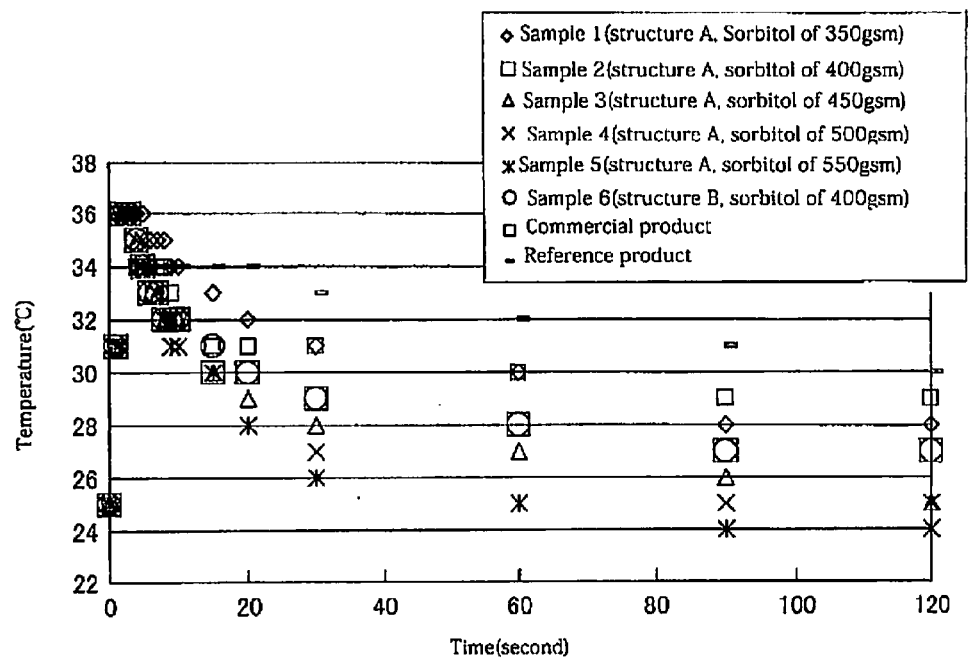
FIG. 13 is a graph of experimental results.
Figure 14:
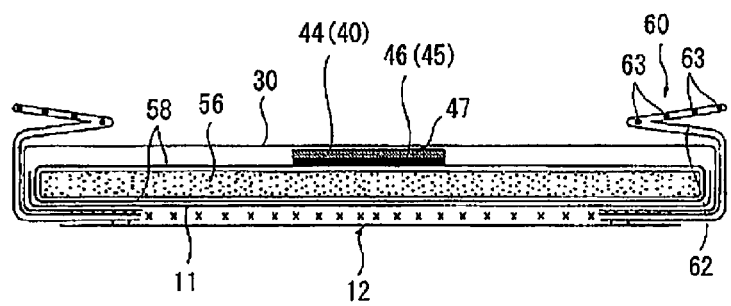
FIG. 14 is a cross-section view of FIG. 1 taken along line 6-6.
Figure 15:
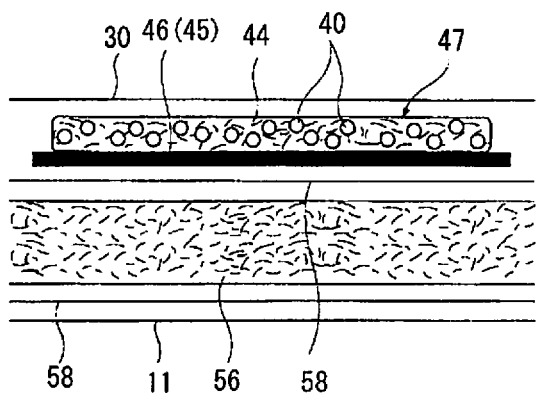
FIG. 15 is a cross-section view of an absorbent main body 10 with an enlarged view of a separate temperature changing member 34.
Figure 16:
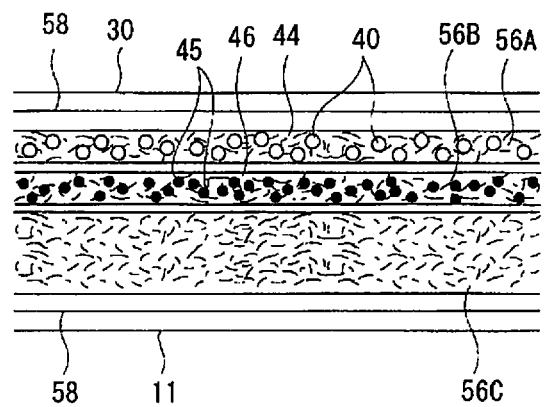
FIG. 16 is a diagram of another embodiment of a structure in relation to temperature change.
Figure 17:
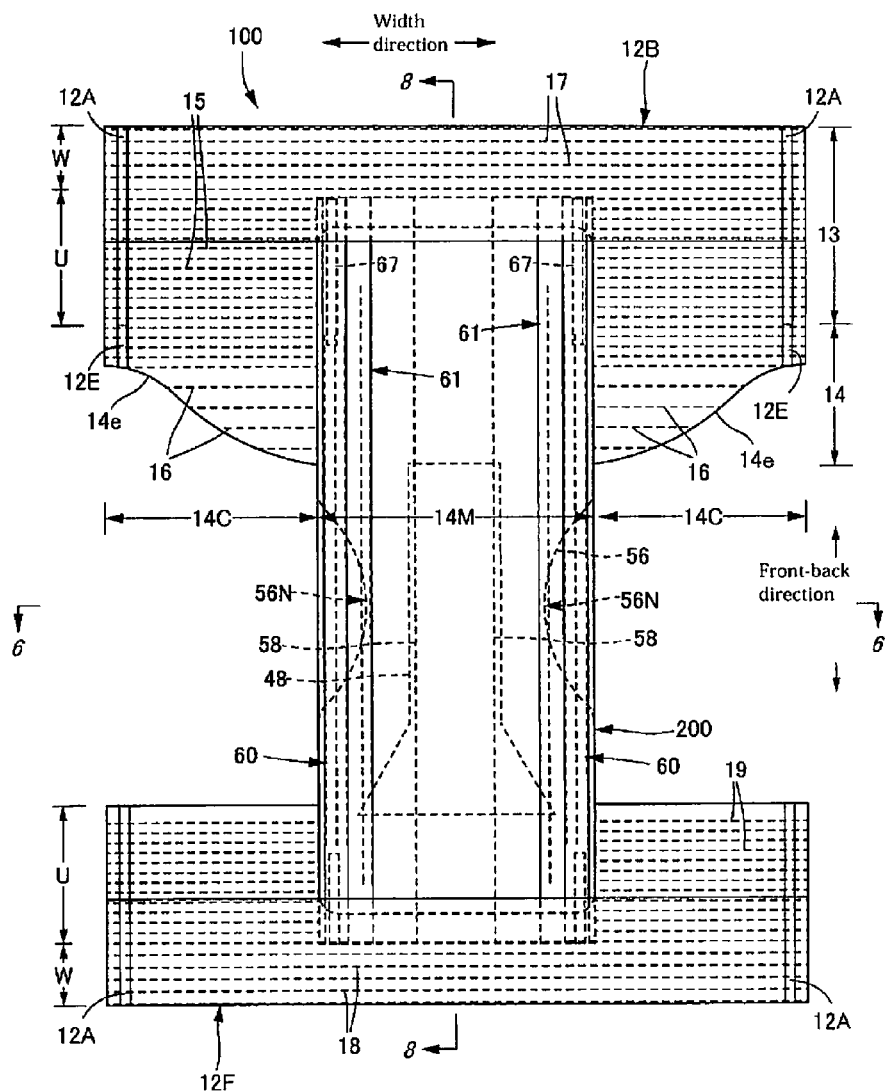
FIG. 17 is a plan view of an inner side of an underpants type disposable diaper in an open state.
Figure 18:
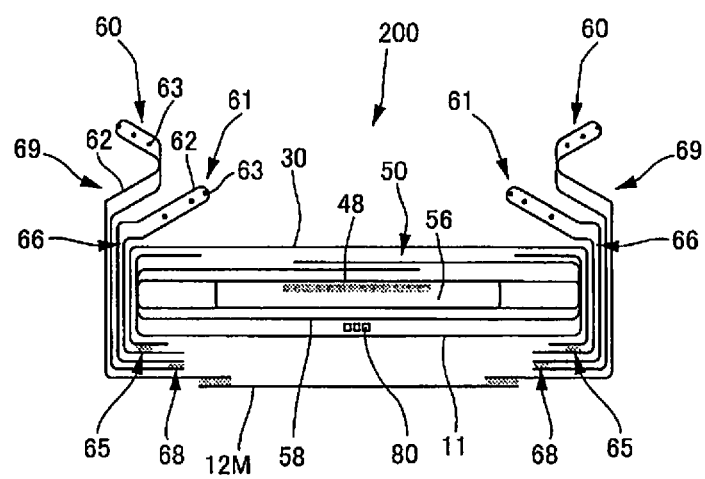
FIG. 18 is a cross-section view of FIG. 17 taken along line 6-6.
Figure 19:
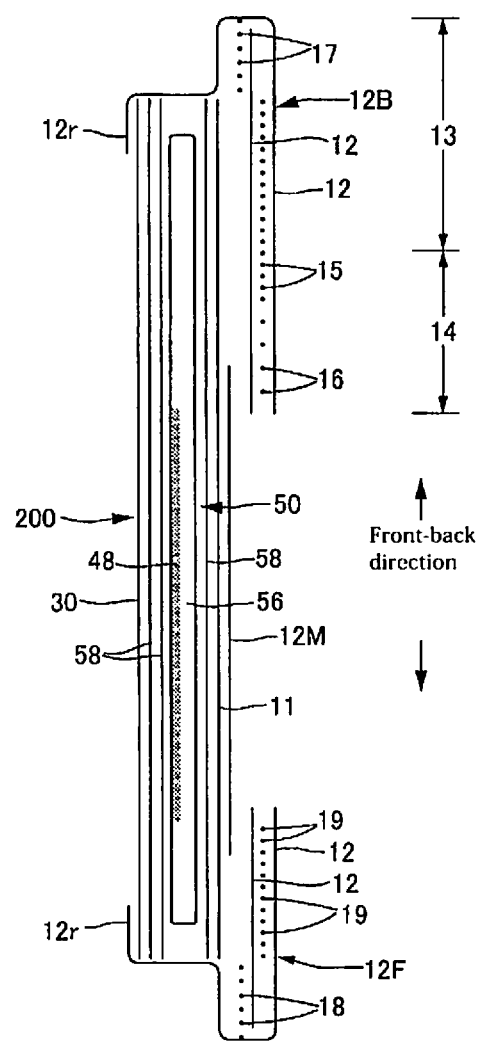
FIG. 19 is a cross-section view of FIG. 17 taken along line 8-8.
Figure 20:
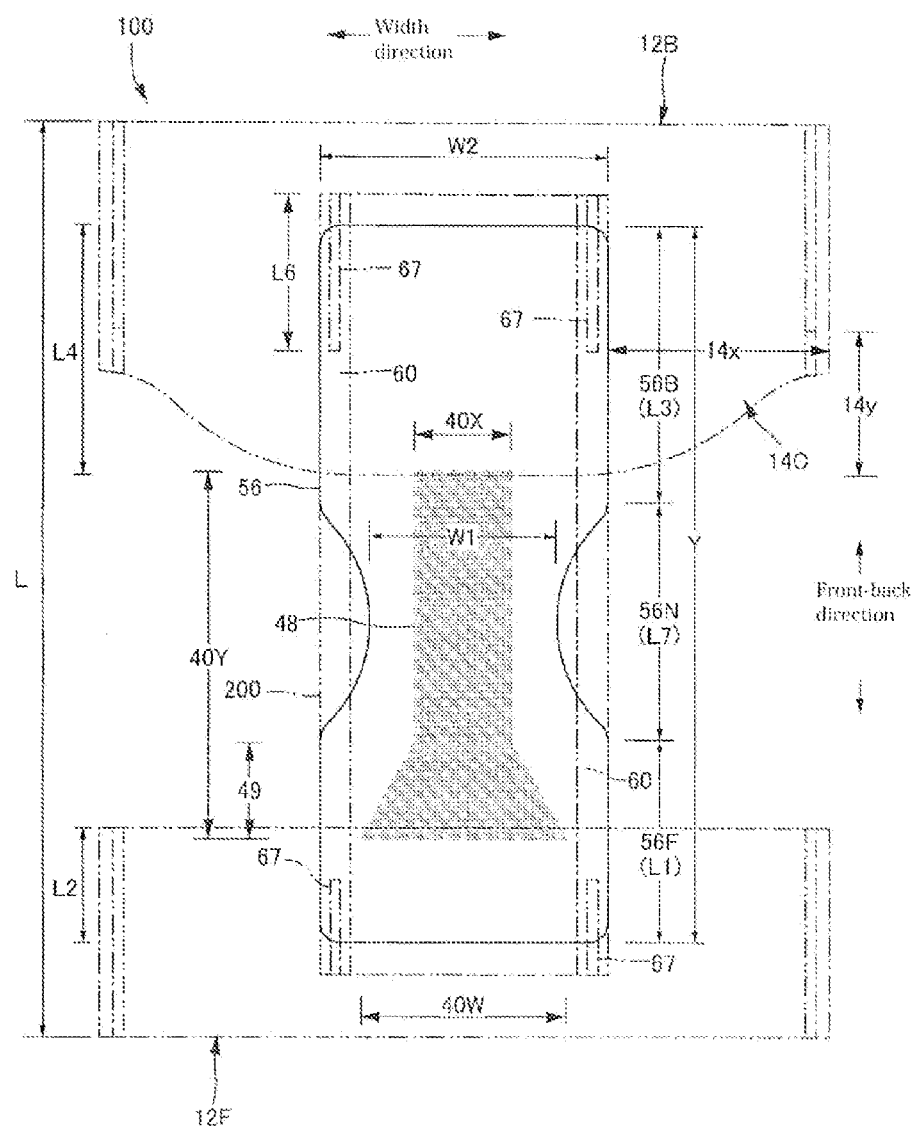
FIG. 20 is a plan view of major components with dimensions of the underpants type disposable diaper in the open state.
Figure 21:
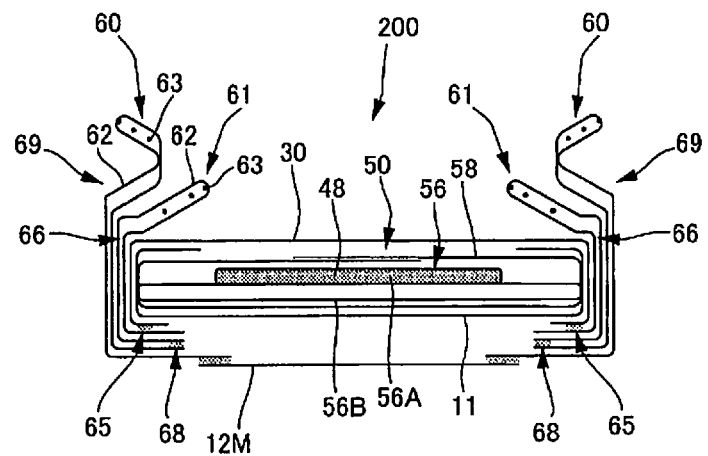
FIG. 21 is a cross-section view of major components of another embodiment.
Figure 22:
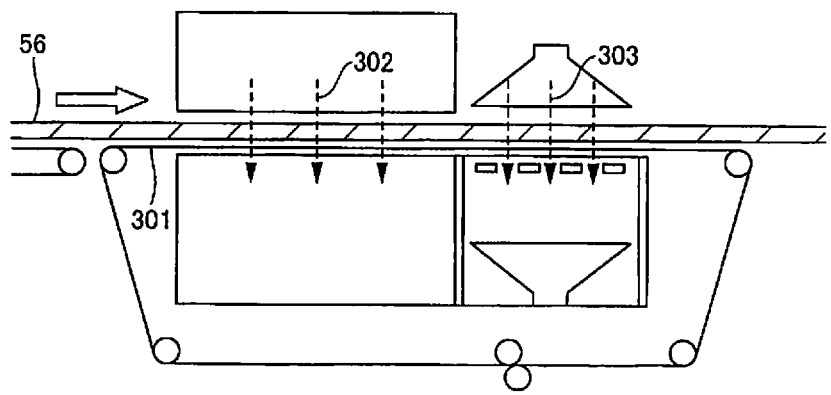
FIG. 22 is a schematic view of a heating means.
Figure 23:
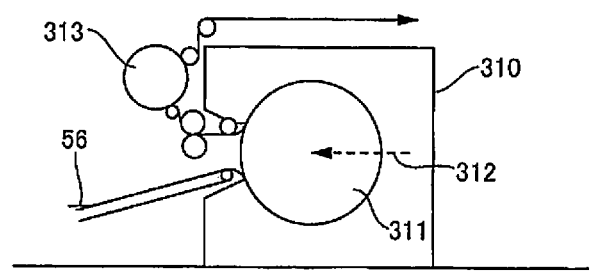
FIG. 23 is a schematic view of a heating means.
Figure 23:
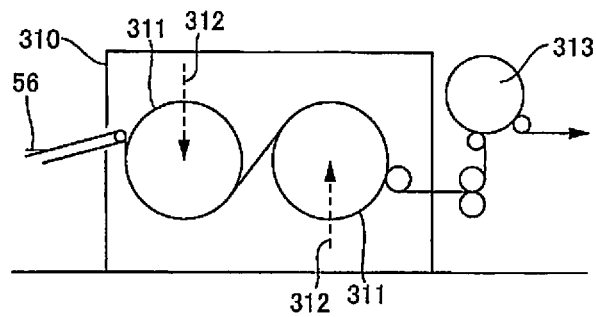
Figure 24:
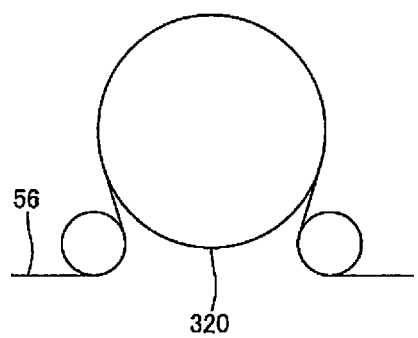
FIG. 24 is a schematic view of a heating means.
Figure 25:
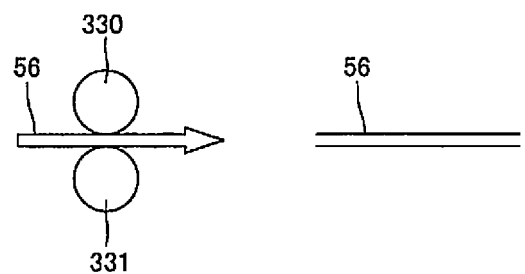
FIG. 25 is a schematic view of a heating means.
Figure 25:
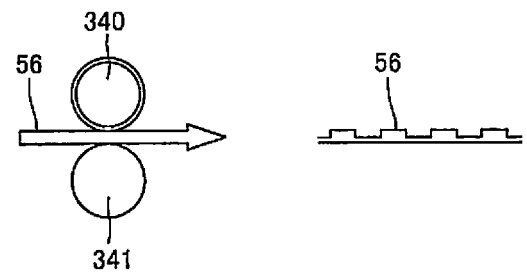
Figure 26:
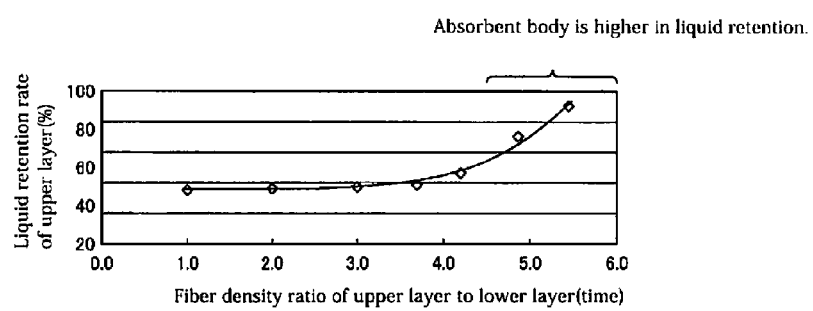
FIG. 26 is a graph of experimental results.
Figure 27:
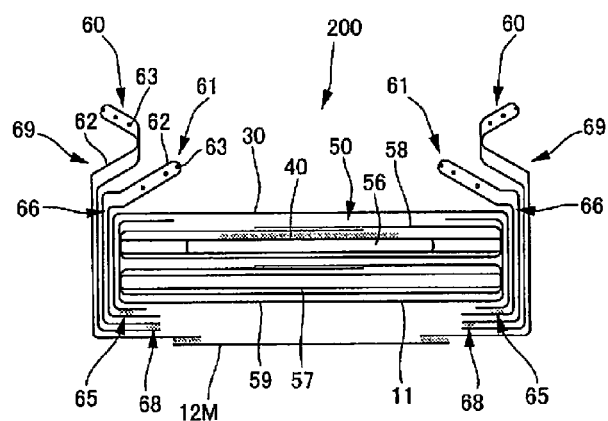
FIG. 27 is a cross-section view of FIG. 1 taken along line 6-6.
Figure 28:
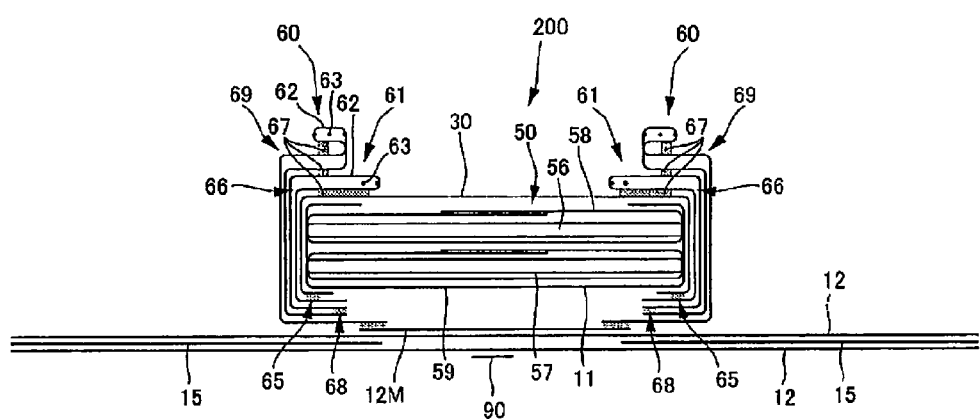
FIG. 28 is a cross-section view of FIG. 1 taken along line 7-7.
Figure 29:
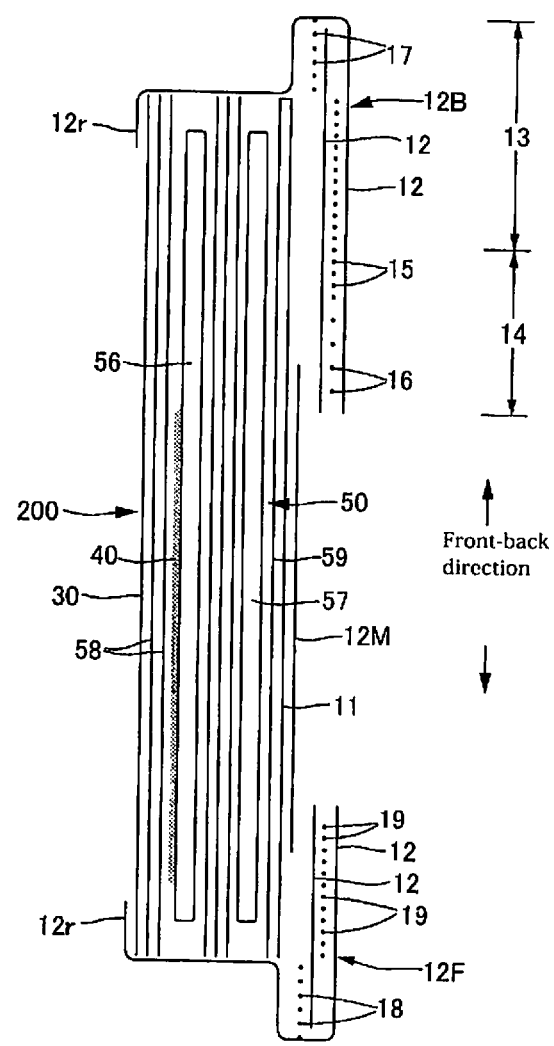
FIG. 29 is a cross-section view of FIG. 1 taken along line 8-8.
Figure 30:
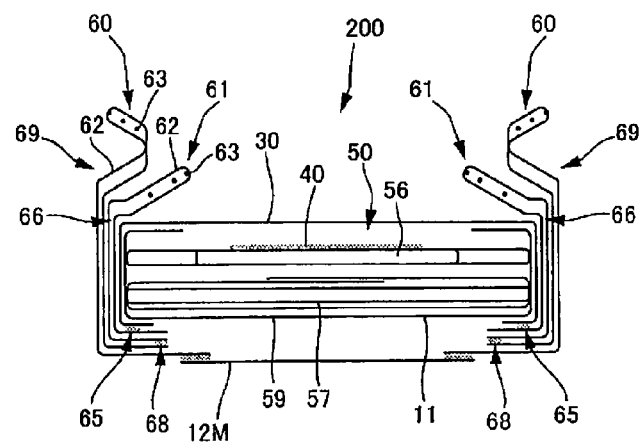
FIG. 30 is a cross-section view of major components of another embodiment.
Figure 31:
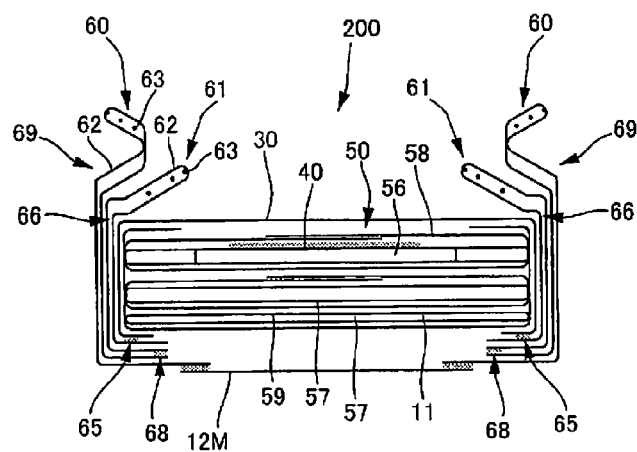
FIG. 31 is a cross-section view of major components of still another embodiment.
Figure 32:
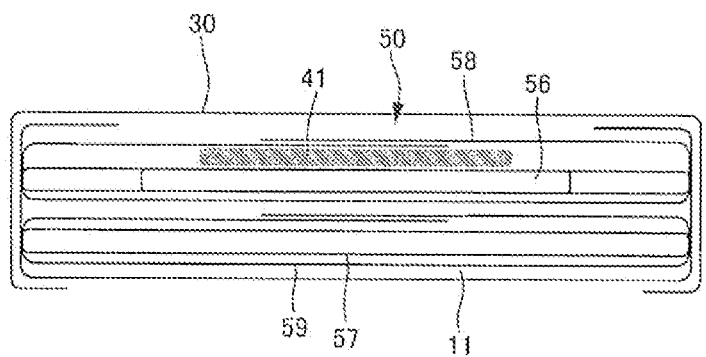
FIG. 32 is a cross-section view of major components of still another embodiment.
Figure 33:
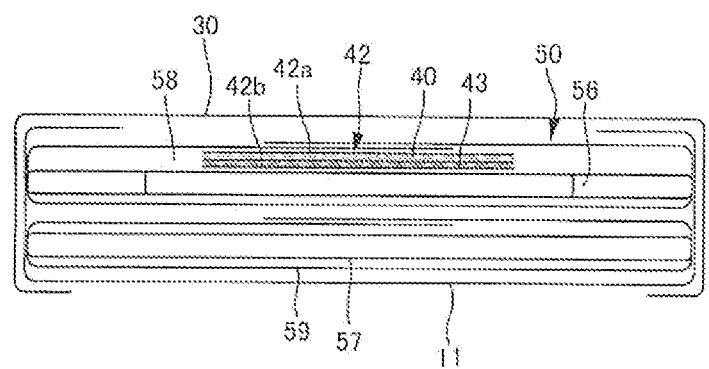
FIG. 33 is a cross-section view of major components of still another embodiment.
Figure 34:
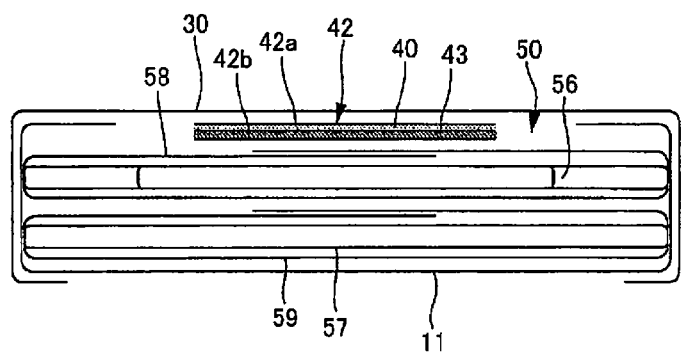
FIG. 34 is a cross-section view of major components of still another embodiment.
Figure 35:
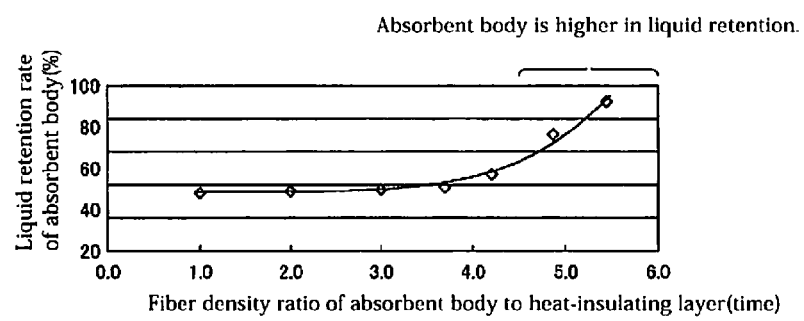
FIG. 35 is a graph of experimental results.
Figure 36:
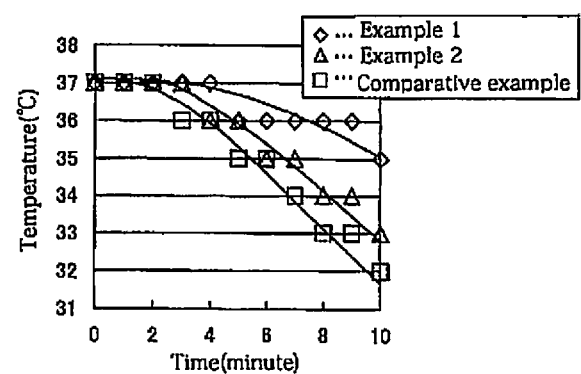
FIG. 36 is a graph of experimental results.

100 . . . Abdomen portion, 11 . . . Liquid impervious sheet, 12F . . . Ventral side outer sheet, 12B . . . Back side outer sheet, 200 . . . Inner body, 30 . . . Face sheet, 40 . . . Temperature changing substance, 50 . . . Absorbent structure, 52 . . . Fiber, 54 . . . High-absorbent polymer particle, 56 . . . Absorbent body, 58 . . . Absorbent body covering sheet, 60 . . . Side barrier cuff, 62 . . . Barrier sheet, 70 . . . Back side elastic sheet.

The invention claimed is:

1. A disposable absorbent article, comprising, at an area including a crotch portion, an absorbent portion which has a liquid pervious face sheet, a backside sheet and an absorbent structure that is interposed therebetween and that is formed by covering an absorbent body made of a high absorbent polymer and a fiber aggregate by an absorbent body covering sheet wherein between the absorbent body and the liquid pervious face sheet, a temperature changing layer is provided that contains a high absorbent polymer and a temperature changing substance for cooling or heating urine by contact with the urine, where the high absorbent polymer is separate and distinct from the temperature changing substance, and where the high absorbent polymer has a water absorption speed of 50 seconds or less, or the absorbent body is higher in density of the high absorbent polymer at a face side than at a back side, and a temperature changing layer that contains a temperature changing substance for cooling or heating urine by contact with the urine, where the high absorbent polymer is separate and distinct from the temperature changing substance, where the temperature changing layer contacts the face side of the absorbent body, and where the high absorbent polymer has a water absorption speed of 50 seconds or less.

2. The disposable absorbent article according to claim 1, wherein a periphery of a part having the temperature changing substance is separated from a periphery of the absorbent body and closer to a central side, and the part includes a portion having the high absorbent polymer at least on one of front-back-direction sides and width-direction sides thereof.

3. The disposable absorbent article according to claim 2, wherein the liquid pervious face sheet is formed by a nonwoven fabric with a thickness of 0.5 mm or less and a basis weight of 10 to 40 g/m$^2$;

the absorbent body covering sheet is formed by crepe paper or a nonwoven fabric with a thickness of 0.2 mm or less and a basis weight of 5 to 25 g/m$^2$;

no other member exists at least at a part overlapping the part having the high absorbent polymer between the liquid pervious face sheet and the temperature changing layer;

the temperature changing substance cools urine by dissolving into the urine and causing an endothermic reaction, and has a solubility of 30 g or more in water of 100 ml at a temperature of 20° C. of 100 ml at a temperature of 20° C.;

the temperature changing substance has a basis weight of 300 to 800 g/m$^2$;

the part having the temperature changing substance has an area of 2,500 to 20,000 mm$^2$;

the temperature changing substance is capable of causing a total amount of change of heat quantity of 50 cal or more to the absorbent body;

the part having the temperature changing substance has a rate of change of heat quantity per unit area of 1 cal/cm$^2$ or more;

the high absorbent polymer has a water absorption speed of 40 seconds or less;

the high absorbent polymer has a basis weight of 50 to 400 g/m$^2$; and the part having the high absorbent polymer has an area of 2,500 to 20,000 mm$^2$.

4. The disposable absorbent article according to claim 3, wherein a layer containing a water-soluble substance is provided as a lower layer below the temperature changing layer.

5. The disposable absorbent article according to claim 4, wherein the layer containing the water-soluble substance is constituted by a formed body mainly made from the water-soluble substance.

6. The disposable absorbent article according to claim 5, wherein the layer containing the water-soluble substance is constituted by a liquid pervious sheet-like object with the water-soluble substance supported.

7. The disposable absorbent article according to claim 3, wherein, out of a central portion of the absorbent body in the width direction, the temperature changing substance is welded to at least a part ranging from the crotch portion to the ventral side portion, and the temperature changing substance is not welded around the temperature changing substance welded part of the absorbent body.

8. The disposable absorbent article according to claim 7, wherein assuming that a product length defined as a front-back direction length ranging from the waist end edge of the ventral side portion to the waist end edge of the back side portion of the absorbent article in an open state is designated as L, the absorbent body is provided at least in a range of 0.15 to 0.80L from the waist side end edge of the ventral side portion to the crotch side, and the temperature changing substance-welded part is provided at least in a range of 0.25 to 0.45L from the waist side end edge of the ventral side portion to the crotch side.

9. The disposable absorbent article according to claim 8, wherein the temperature changing substance-welded part is shaped along the groin portion of a wearer so as to be wider than the groin portion and be further wider with increasing proximity to the waist side.

10. The disposable absorbent article according to claim 9, wherein the crotch portion of the absorbent body has a narrower portion along the legs, and if it is assumed that the absorbent body in an open state has a front-back direction length Y and a width X, the narrower portion has a front-back direction length of 0.2 to 0.3Y and a narrowest part of the narrower portion has a width of 0.6 to 0.75X, the waist side end edge of the temperature changing substance-welded part in the ventral side portion has a width of 0.4 to 0.7X, a crotch side end of the further wider portion of the temperature changing substance-welded part is located at the same position as the narrowest part of the narrower portion or is located closer to the ventral side than the former position, and a back end of the temperature changing substance-welded part is located at the same position as a back end of the narrower portion or is located closer to the back side than the former position, and the back end has a width of 0.7 times or less the width of the waist side end edge of the temperature changing substance-welded part in the ventral side portion, and the width is 0.5X or less.

11. The disposable absorbent article according to claim 3, wherein a heat-insulating layer is disposed between the absorbent structure and the backside sheet.

12. The disposable absorbent article according to claim 11, wherein the absorbent body is formed by a fiber aggregate with a fiber density of 2.25 to 6.75 g/m$^3$, the heat-insulating layer is formed by a fiber aggregate with a fiber density of 0.5 to 1.5 g/m$^3$, and the fiber density of the absorbent body is 4.5 times or more the fiber density of the heat-insulating layer.

13. The disposable absorbent article according to claim 12, wherein separately from the absorbent body, the heat-insulating layer is covered with a heat-insulating layer covering sheet made of a fiber aggregate with a higher fiber density than that of the heat-insulating layer.

14. The disposable absorbent article according to claim 13, wherein the heat-insulating layer covers an area of 50% or more of the backside surface of the absorbent body.

15. A disposable absorbent article, comprising, at an area including a crotch portion, an absorbent portion which has a liquid pervious face sheet, a backside sheet and an absorbent structure that is interposed therebetween and that is formed by covering an absorbent body made of a high absorbent polymer and a fiber aggregate by an absorbent body covering sheet wherein the absorbent body is higher in density of the high absorbent polymer at a face side than at a back side, and has a temperature changing layer that contains a temperature changing substance for cooling or heating urine by contact with the urine, where the high absorbent polymer is separate and distinct from the temperature changing substance, where the temperature changing layer contacts the face side of the absorbent body, and where the high absorbent polymer has a water absorption speed of 50 seconds or less.

16. A disposable absorbent article, comprising, at an area including a crotch portion, an absorbent portion which has a liquid pervious face sheet, a backside sheet and an absorbent structure that is interposed therebetween and that is formed by covering an absorbent body made of a high absorbent polymer and a fiber aggregate by an absorbent body covering sheet wherein between the absorbent body and the liquid pervious face sheet, a temperature changing layer is provided that contains a high absorbent polymer and a temperature changing substance for cooling or heating urine by contact with the urine, where the high absorbent polymer is separate and distinct from the temperature changing substance, and where the high absorbent polymer has a water absorption speed of 50 seconds or less.

17. The article of claim 15, where the high absorbent polymer is selected from the group consisting of starch-acrylic acid (salt) graft copolymer, saponified product of starch-acrylonitrile copolymer, cross-linked sodium carboxymethyl cellulose, and acrylic acid (salt) polymer.

18. The article of claim 16, where the high absorbent polymer is selected from the group consisting of starch-acrylic acid (salt) graft copolymer, saponified product of starch-acrylonitrile copolymer, cross-linked sodium carboxymethyl cellulose, and acrylic acid (salt) polymer.

19. The article of claim 17, where the temperature changing substance is selected from the group consisting of hydrate salts, anhydrous salts, urea, sugar alcohols, aluminum chloride, aluminum sulfide, and aluminum potassium sulfate.

20. The article of claim 18, where the temperature changing substance is selected from the group consisting of hydrate salts, anhydrous salts, urea, sugar alcohols, aluminum chloride, aluminum sulfide, and aluminum potassium sulfate.

* * * * *